United States Patent [19]
Cordell et al.

[11] Patent Number: 5,187,153
[45] Date of Patent: Feb. 16, 1993

[54] METHODS OF TREATMENT USING ALZHEIMER'S AMYLOID POLYPEPTIDE DERIVATIVES

[75] Inventors: Barbara Cordell; James W. Schilling, both of Palo Alto, Calif.; Nobuhiko Katunuma, Tokushima, Japan

[73] Assignee: Scios Nova Inc., Mountain View, Calif.

[21] Appl. No.: 502,273

[22] Filed: Mar. 29, 1990

Related U.S. Application Data

[63] Continuation-in-part of Ser. No. 361,912, Jun. 6, 1989, which is a continuation of Ser. No. 359,911, May 12, 1989, abandoned, which is a continuation-in-part of Ser. No. 87,002, Aug. 18, 1987, abandoned, which is a continuation-in-part of Ser. No. 8,810, Jan. 30, 1987, abandoned, which is a continuation-in-part of Ser. No. 948,376, Dec. 31, 1986, abandoned, which is a continuation-in-part of Ser. No. 932,193, Nov. 17, 1986, abandoned.

[51] Int. Cl.$^5$ ............................................. A61K 37/64
[52] U.S. Cl. ...................................... 514/12; 530/324; 930/250; 514/2; 424/94.64
[58] Field of Search .................... 514/12; 530/324; 435/69.7; 900/250

[56] References Cited

U.S. PATENT DOCUMENTS

| | | | |
|---|---|---|---|
| 4,595,674 | 6/1986 | Tschesche et al. | 514/09 |
| 4,666,829 | 5/1987 | Glenner et al. | |
| 4,912,206 | 3/1990 | Goldgaber et al. | 536/27 |

OTHER PUBLICATIONS

Carrell, *Nature* vol. 331, pp. 3478–479, 1988.
Tanzi et al., *Nature* vol. 331, pp. 528–530, 1988.
Robakis et al., *Proc Natl Acad Sci U.S.A.* 84:4190–4194 (Jun. 1987).
Kang et al., *Nature* 325:733–736 (19 Feb. 1987).
Goldgaber et al., *Science* 235:877–880 (Feb. 1987).
Neve et al., *Biological Abstracts* 83(f):1987.
Tanzi et al., *Science* 235:880–884 (Feb. 1987).
Masters et al., *Chemical Abstracts* 104(15) (Apr. 1986), pp. 506–507.
Masters et al., *EMBO J* 4(1):2757–2763 (1985).
Uzan et al., *Biochem Biophys Res Comm* 119:273–281 (Feb. 1984).
Masters et al., *Proc Natl Acad Sci U.S.A.* 82:4245–4249 (Jun. 1985).
Glenner and Wong, *Biochem Biophys Res Comm* 120(3):885–890 (May 1984).
Glenner et al., *Biochem Biophys Res Comm* 122:1131–1135 (Aug. 1984).
Glenner et al., "Amyloidosis", published by Plenum Press, Jun. 1986, pp. 693–701.
Roher et al., *Proc Natl Acad Sci U.S.A.* 82:2662–2666 (Apr. 1986).
Wong et al., *Proc Natl Acad Sci U.S.A.* 82:8729–8732 (Dec. 1985).

(List continued on next page.)

*Primary Examiner*—Garnette D. Draper
*Assistant Examiner*—Nina Ossanna
*Attorney, Agent, or Firm*—Morrison & Foerster

[57] ABSTRACT

Pharmaceutical compositions containing a 57 amino acid protease inhibitor and uses for those compositions are taught. The protease inhibitor is referred to as A4i which is associated with Alzheimer's disease. In addition to the A4i protease, other analogs are taught as are pharmaceutical compositions containing such analogs and their uses in treating a variety of abnormalities associated with Kunitz-type basic protease inhibitors. For example, it has been found that pharmaceutical compositions containing A4i protease and analogs thereof inhibit plasmin and tryptase, and also inhibit pancreatic trypsin, alpha-chymotrypsin, tissue kallikrein and serum kallikrein. In that certain diseases are associated with a general release of proteases such as trypsin, chymotrypsin and elastase into the circulatory system pharmaceutical compositions containing A4i and analogs thereof can be used in the management of such diseases.

3 Claims, 25 Drawing Sheets

OTHER PUBLICATIONS

Ohtsuka et al., *biol Chem* 269:2605–2608 (Mar. 1985).
Takahashi et al., *Proc Natl Acad Sci U.S.A.* 82:1931–1935 (Apr. 1985).
Robakis et al., *Proc Natl Acad Sci U.S.A.* 83:6377–6381 (1986).
Allsop et al., *Neuroscience Letters* 68:252–256 (1986).
Price et al., *Drug Development Res* 5:59–68 (1985).
Delabar et al., *Science* 235:1390–1392 (1987).
Barnes, *Science* 235:846–847 (1987).
Anderton, *Nature* 325:658–659 (1987).
Selkoe et al., *Science* 235:873–876 (1987).
Allsop et al., *Brain Res* 259:348–352 (1983).
Westermark and Cornwell, *Amyloidosis*, pp. 659–668 (1984).
Allsop et al., *Amyloidosis*, pp. 723–732 (1984).
St. George-Hyslop et al., *Science* 235:885–890 (1987).
Ponte et al., *Nature* 331:530–532 (1988).
Kitaguchi et al., *Nature* 331:530–532 (1988).
Shivers et al., EMBO J 7(5):1365–1370 (1988).
Dyrks et al., *EMBO J* 7(4):949–957 (1988).
Marks et al., *J. Biol Chem* 261(16):7115–7118 (1986).
Tan and Kaiser, *Biochem* 16(8):1531–1541 (1977).
Gebhard et al., *Protease Inhibitors*, Barrett and Salvesen (eds.), 1986, Elsevier Science Publishers BV, pp. 375–388.
Fritz and Wunderer, *Drug Res* 33(1):479–494 (1983).

```
                                                                ATG CTG CCC
                                                                MET Leu Pro

GGT TTG GCA CTG CTC CTG CTG GCC GCC TGG ACG GCT CGG GCG CTG GAG GTA CCC
Gly Leu Ala Leu Leu Leu Leu Ala Ala Trp Thr Ala Arg Ala Leu Glu Val Pro
                        10                                      20

ACT GAT GGT AAT GCT GGC CTG CTG GCT GAA CCC CAG ATT GCC ATG TTC TGT GGC
Thr Asp Gly Asn Ala Gly Leu Leu Ala Glu Pro Gln Ile Ala MET Phe Cys Gly
                        30

AGA CTG AAC ATG CAC ATG AAT GTC CAG AAT GGG AAG TGG GAT TCA GAT CCA TCA
Arg Leu Asn MET His MET Asn Val Gln Asn Gly Lys Trp Asp Ser Asp Pro Ser 40                                      50
GGG ACC AAA ACC TGC ATT GAT ACC AAG GAA GGC ATC CTG CAG TAT TGC CAA GAA
Gly Thr Lys Thr Cys Ile Asp Thr Lys Glu Gly Ile Leu Gln Tyr Cys Gln Glu
            60                                      70

GTC TAC CCT GAA CTG CAG ATC ACC AAT GTG GTA GAA GCC AAC CAA CCA GTG ACC
Val Tyr Pro Glu Leu Gln Ile Thr Asn Val Val Glu Ala Asn Gln Pro Val Thr
                    80                                      90

ATC CAG AAC TGG TGC AAG CGG GGC CGC AAG CAG TGC AAG ACC CAT CCC CAC TTT
Ile Gln Asn Trp Cys Lys Arg Gly Arg Lys Gln Cys Lys Thr His Pro His Phe
                        100                                     110

GTG ATT CCC TAC CGC TGC TTA GTT GGT GAG TTT GTA AGT GAT GCC CTT CTC GTT
Val Ile Pro Tyr Arg Cys Leu Val Gly Glu Phe Val Ser Asp Ala Leu Leu Val
                            120

CCT GAC AAG TGC AAA TTC TTA CAC CAG GAG AGG ATG GAT GTT TGC GAA ACT CAT
Pro Asp Lys Cys Lys Phe Leu His Gln Glu Arg MET Asp Val Cys Glu Thr His
130                                     140

CTT CAC TGG CAC ACC GTC GCC AAA GAG ACA TGC AGT GAG AAG AGT ACC AAC TTG
Leu His Trp His Thr Val Ala Lys Glu Thr Cys Ser Glu Lys Ser Thr Asn Leu
            150                                     160

CAT GAC TAC GGC ATG TTG CTG CCC TGC GGA ATT GAC AAG TTC CGA GGG GTA GAG
His Asp Tyr Gly MET Leu Leu Pro Cys Gly Ile Asp Lys Phe Arg Gly Val Glu
                    170                                     180

TTT GTG TGT TGC CCA CTG GCT GAA GAA AGT GAC AAT GTG GAT TCT GCT GAT GCG
Phe Val Cys Cys Pro Leu Ala Glu Glu Ser Asp Asn Val Asp Ser Ala Asp Ala
                        190                                     200
```

FIG. 1-1

```
GAG GAG GAT GAC TCG GAT GTC TGG TGG GGC GGA GCA GAC ACA GAC TAT GCA GAT
Glu Glu Asp Asp Ser Asp Val Trp Trp Gly Gly Ala Asp Thr Asp Tyr Ala Asp
                            210

GGG AGT GAA GAC AAA GTA GTA GAA GTA GCA GAG GAG GAA GAA GTG GCT GAG GTG
Gly Ser Glu Asp Lys Val Val Glu Val Ala Glu Glu Glu Glu Val Ala Glu Val
220                                     230

GAA GAA GAA GAA GCC GAT GAT GAC GAG GAC GAT GAG GAT GGT GAT GAG GTA GAG
Glu Glu Glu Glu Ala Asp Asp Asp Glu Asp Asp Glu Asp Gly Asp Glu Val Glu
            240                                     250

GAA GAG GCT GAG GAA CCC TAC GAA GAA GCC ACA GAG AGA ACC ACC AGC ATT GCC
Glu Glu Ala Glu Glu Pro Tyr Glu Glu Ala Thr Glu Arg Thr Thr Ser Ile Ala
                    260                                     270

ACC ACC ACC ACC ACC ACC ACA GAG TCT GTG GAA GAG GTG GTT CGA GAG GTG TGC
Thr Thr Thr Thr Thr Thr Thr Glu Ser Val Glu Glu Val Val Arg Glu Val Cys
                        280                                     290

TCT GAA CAA GCC GAG ACG GGG CCG TGC CGA GCA ATG ATC TCC CGC TGG TAC TTT
Ser Glu Gln Ala Glu Thr Gly Pro Cys Arg Ala MET Ile Ser Arg Trp Tyr Phe
                                300

GAT GTG ACT GAA GGG AAG TGT GCC CCA TTC TTT TAC GGC GGA TGT GGC GGC AAC
Asp Val Thr Glu Gly Lys Cys Ala Pro Phe Phe Tyr Gly Gly Cys Gly Gly Asn
 310                                        320

CGG AAC AAC TTT GAC ACA GAA GAG TAC TGC ATG GCC GTG TGT GGC AGC GCC ATT
Arg Asn Asn Phe Asp Thr Glu Glu Tyr Cys MET Ala Val Cys Gly Ser Ala Ile
        330                                     340

CCT ACA ACA GCA GCC AGT ACC CCT GAT GCC GTT GAC AAG TAT CTC GAG ACA CCT
Pro Thr Thr Ala Ala Ser Thr Pro Asp Ala Val Asp Lys Tyr Leu Glu Thr Pro
                350                                     360

GGG GAT GAG AAT GAA CAT GCC CAT TTC CAG AAA GCC AAA GAG AGG CTT GAG GCC
Gly Asp Glu Asn Glu His Ala His Phe Gln Lys Ala Lys Glu Arg Leu Glu Ala
                        370                                     380

AAG CAC CGA GAG AGA ATG TCC CAG GTC ATG AGA GAA TGG GAA GAG GCA GAA CGT
Lys His Arg Glu Arg MET Ser Gln Val MET Arg Glu Trp Glu Glu Ala Glu Arg
                            390

CAA GCA AAG AAC TTG CCT AAA GCT GAT AAG AAG GCA GTT ATC CAG CAT TTC CAG
Gln Ala Lys Asn Leu Pro Lys Ala Asp Lys Lys Ala Val Ile Gln His Phe Gln
400                                     410

GAG AAA GTG GAA TCT TTG GAA CAG GAA GCA GCC AAC GAG AGA CAG CAG CTG GTG
Glu Lys Val Glu Ser Leu Glu Gln Glu Ala Ala Asn Glu Arg Gln Gln Leu Val
            420                                     430
```

FIG. 1-2

```
GAG ACA CAC ATG GCC AGA GTG GAA GCC ATG CTC AAT GAC CGC CGC CGC CTG GCC
Glu Thr His MET Ala Arg Val Glu Ala MET Leu Asn Asp Arg Arg Arg Leu Ala
            440                                     450

CTG GAG AAC TAC ATC ACC GCT CTG CAG GCT GTT CCT CCT CGG CCT CGT CAC GTG
Leu Glu Asn Tyr Ile Thr Ala Leu Gln Ala Val Pro Pro Arg Pro Arg His Val
                    460                                         470

TTC AAT ATG CTA AAG AAG TAT GTC CGC GCA GAA CAG AAG GAC AGA CAG CAC ACC
Phe Asn MET Leu Lys Lys Tyr Val Arg Ala Glu Gln Lys Asp Arg Gln His Thr
                            480

CTA AAG CAT TTC GAG CAT GTG CGC ATG GTG GAT CCC AAG AAA GCC GCT CAG ATC
Leu Lys His Phe Glu His Val Arg MET Val Asp Pro Lys Lys Ala Ala Gln Ile
490                                         500

CGG TCC CAG GTT ATG ACA CAC CTC CGT GTG ATT TAT GAG CGC ATG AAT CAG TCT
Arg Ser Gln Val MET Thr His Leu Arg Val Ile Tyr Glu Arg MET Asn Gln Ser
        510                                     520

CTC TCC CTG CTC TAC AAC GTG CCT GCA GTG GCC GAG GAG ATT CAG GAT GAA GTT
Leu Ser Leu Leu Tyr Asn Val Pro Ala Val Ala Glu Glu Ile Gln Asp Glu Val
            530                                         540

GAT GAG CTG CTT CAG AAA GAG CAA AAC TAT TCA GAT GAC GTC TTG GCC AAC ATG
Asp Glu Leu Leu Gln Lys Glu Gln Asn Tyr Ser Asp Asp Val Leu Ala Asn MET
                        550                                     560

ATT AGT GAA CCA AGG ATC AGT TAC GGA AAC GAT GCT CTC ATG CCA TCT TTG ACC
Ile Ser Glu Pro Arg Ile Ser Tyr Gly Asn Asp Ala Leu MET Pro Ser Leu Thr
                                570

GAA ACG AAA ACC ACC GTG GAG CTC CTT CCC GTG AAT GGA GAG TTC AGC CTG GAC
Glu Thr Lys Thr Thr Val Glu Leu Leu Pro Val Asn Gly Glu Phe Ser Leu Asp
580                                         590

GAT CTC CAG CCG TGG CAT TCT TTT GGG GCT GAC TCT GTG CCA GCC AAC ACA GAA
Asp Leu Gln Pro Trp His Ser Phe Gly Ala Asp Ser Val Pro Ala Asn Thr Glu
        600                                         610

AAC GAA GTT GAG CCT GTT GAT GCC CGC CCT GCT GCC GAC CGA GGA CTG ACC ACT
Asn Glu Val Glu Pro Val Asp Ala Arg Pro Ala Ala Asp Arg Gly Leu Thr Thr
                    620                                     630

CGA CCA GGT TCT GGG TTG ACA AAT ATC AAG ACG GAG GAG ATC TCT GAA GTG AAG
Arg Pro Gly Ser Gly Leu Thr Asn Ile Lys Thr Glu Glu Ile Ser Glu Val Lys
                            640                                     650

ATG GAT GCA GAA TTC CGA CAT GAC TCA GGA TAT GAA GTT CAT CAT CAA AAA TTG
MET Asp Ala Glu Phe Arg His Asp Ser Gly Tyr Glu Val His His Gln Lys Leu
                                660
```

FIG. 1-3

```
GTG TTC TTT GCA GAA GAT GTG GGT TCA AAC AAA GGT GCA ATC ATT GGA CTC ATG
Val Phe Phe Ala Glu Asp Val Gly Ser Asn Lys Gly Ala Ile Ile Gly Leu MET
670                                     680

GTG GGC GGT GTT GTC ATA GCG ACA GTG ATC GTC ATC ACC TTG GTG ATG CTG AAG
Val Gly Gly Val Val Ile Ala Thr Val Ile Val Ile Thr Leu Val MET Leu Lys
        690                                     700

AAG AAA CAG TAC ACA TCC ATT CAT CAT GGT GTG GTG GAG GTT GAC GCC GCT GTC
Lys Lys Gln Tyr Thr Ser Ile His His Gly Val Val Glu Val Asp Ala Ala Val
                710                                     720

ACC CCA GAG GAG CGC CAC CTG TCC AAG ATG CAG CAG AAC GGC TAC GAA AAT CCA
Thr Pro Glu Glu Arg His Leu Ser Lys MET Gln Gln Asn Gly Tyr Glu Asn Pro
                    730                                     740

ACC TAC AAG TTC TTT GAG CAG ATG CAG AAC TAG
Thr Tyr Lys Phe Phe Glu Gln MET Gln Asn
                        750
```

FIG. I-4

```
                                          27                                              54
TTT TTG TTC AAA ATA GGT AGT AAT TGA AGT TTT AAA TAT AGG GTA TCA TTT TTC
Phe Leu Phe Lys Ile Gly Ser Asn  .  Ser Phe Lys Tyr Arg Val           Phe 81                                             108
TTT AAG AGT CAT TTA TCA ATT TTC TTC TAA CTT CAG GCC TAG AAA GAA GTT TTG
Phe Lys Ser His Leu Ser Ile Phe Phe  .  Leu Gln Ala  .  Lys Glu Val Leu 135                                             162
GGT AGG CTT TGT CTT ACA GTG TTA TTA TTT ATG AGT AAA ACT AAT TGG TTG TCC
Gly Arg Leu Cys Leu Thr Val Leu Leu Phe MET Ser Lys Thr Asn Trp Leu Ser

Hind II
                                         189|                    ↓                       216
TGC ATA CTT TAA TTA TGA TGT AAT ACA|GGT TCT GGG TTG ACA AAT ATC AAG ACG
Cys Ile Leu  .  Leu  .  Cys Asn Thr|Gly Ser Gly Leu Thr Asn Ile Lys Thr Eco RI
                                         243          ↓                                  270
GAG GAG ATC TCT GAA GTG AAG ATG GAT GCA GAA TTC CGA CAT GAC TCA GGA TAT
Glu Glu Ile Ser Glu Val Lys MET Asp Ala Glu Phe Arg His Asp Ser Gly Tyr
                                      1                    5                       10
                               Rsa I ↓
                                         |297                                            324
GAA GTT CAT CAT CAA AAA TTG GTA|CGT AAA ATA ATT TAC CTC TTT CCA CTA CTG
Glu Val His His Gln Lys Leu Val|Arg Lys Ile Ile Tyr Leu Phe Pro Leu Leu
                       15           18|

351                                             378
TTT GTC TTG CCA AAT GAC CTA TTA ACT CTG GTT CAT CCT GTG CTA GAA ATC AAA
Phe Val Leu Pro Asn Asp Leu Leu Thr Leu Val His Pro Val Leu Glu Ile Lys 405                                             432
TTA AGG AAA AGA TAA AAA TAC AAT GCT TGC CTA TAG GAT TAC CAT GAA AAC ATG
Leu Arg Lys Arg  .  Lys Tyr Asn Ala Cys Leu  .  Asp Tyr His Glu Asn MET 459                                             486
AAG AAA ATA AAT AGG CTA GGC TGA GCG CAG TGG CTC AAG CCT GTA ATC CCA GCA
Lys Lys Ile Asn Arg Leu Gly  .  Ala Gln Trp Leu Lys Pro Val Ile Pro Ala
```

```
          10         20         30         40         50         60         70
GAATTCCCCT GGGAGCCAAA GGAATTGGGA ATGTGTAGCC CAAGTAAGAC AAGAACCAGC AGGAACATGC
          80         90        100        110        120        130        140
CTCTCCTTAG GGTCGTGATA CCTGTTCAAG GTTTTAATGT ATTAGGCTTG CTCTGTGTTG
         150        160        170        180        190        200        210
AATCAGGCTC AAAGGATGGA AGTTACAGGG AAGCTGATTC TGGCTTCATG TAAAAAAAGG ACAGTTGGG
         220        230        240        250        260        270        280
CAGGCAAATC TATCAAAAAA TGGAGGGAAA TTGATACATT CCTCTATGTT CAAACAGGAA CTGACAATCT
         290        300        310        320        330        340        350
GCCCCTGGGT GGGAACACGG TAGAGAAGAT GACTTCAAAA GCCCTTTTCA TCCTAAAATT CTGATGTTTG
         360        370        380        390        400        410        420
ATAATTAAAT GTTATAGAGT GGACACTGAT ATTTACATTT TTTGAATAAT TTTTTGGTTT TTAAATGACT
         430        440        450        460        470        480        490
CTGCATTTTG TTTTAAGCTT CAAATTATTA TCGTAGGTTA GAAATTCATC AGAACAATTA GTGTTAAGAA
         500        510        520        530        540        550        560
TCATATAGCA ATTTATAGAA AAGGAAGAGT TCGTAGGTTA TAAATTCTGT TAGTTGCTAA GAAGCATTTT
         570        580        590        600        610        620        630
TAAAATTATG TACTATAGCT CTTTATTCAG CAGACGAACC AATTACAAATC TGTGTAACTA GAACACTTGA
```

FIG. 3-2

```
     640         650         660         670         680         690         700
CTAAAATTAT ATAATTTTTA CAACGCTTCA CTGCATAGAT ACATGAACAT AATTTATTTG TAATTGAAC 710         720         730         740         750         760         770
AAAGCCCCAA AGTAGCAGTT TTGTTCTACC AGGTAATTAA TGCTCATTTT TAAAGCCTTT TATTATTATT 780         790         800         810         820         830         840
TCTGAAGTAA TGAGTGCACA TGGAAAAAGA CACATATATAG GCTAAACAAT AAGCCCGTAA GCCAAGCCAA 850         860         870         880         890         900         910
CATATTCCAG GAACAAATCC TTGCCAACCT CTCAACCAGG ATTTAACTTC TGCTTTTCCC CCATTTTCAA 920         930         940         950         960         970         980
AAATTATAGC ATGTATTTAA AGGCAGCAGA AGCCTTACTT TCAGGTTTCC CTTACCCTTT CATTTCTTTT 990         1000        1010        1020        1030        1040        1050
TGTTCAAAAT AGGTAGTAAT TGAAGTTTTA AATATAGGGT ATCATTTTTC TTTAAGAGTC ATTTATCAAT 1060        1070        1080        1090        1100        1110        1120
TTTCTTCTAA CTTCAGGCCT AGAAAGAAGT TTTGGGTAGG CTTTGTCTTA CAGTGTTATT ATTTATGAGT 1130        1140        1150        1160        1170        1180        1190
AAAACTAATT GGTTGTCCTG CATACTTTAA TTATGATGTA ATACAGGTTC TGGGTTGACA AATATCAAGA 1200        1210                                1228
CGGAGGAGAT CTCTGAAGTG AAG ATG GAT GCA GAA TTC
                         MET Asp Ala Glu Phe
                          1    2   3   4
```

FIG. 4-1

```
GAA TTC CGA CAT GAC TCA GGA TAT GAA GTT CAT CAT CAA AAA TTG GTG TTC TTT
Glu Phe Arg His Asp Ser Gly Tyr Glu Val His His Gln Lys Leu Val Phe Phe
  3                          10                                      20

GCA GAA GAT GTG GGT TCA AAC AAA GGT GCA ATC ATT GGA CTC ATG GTG GGC GGT
Ala Glu Asp Val Gly Ser Asn Lys Gly Ala Ile Ile Gly Leu MET Val Gly Gly
                             30

GTT GTC ATA GCG ACA GTG ATC GTC ATC ACC TTG GTG ATG CTG AAG AAA AAA CAG
Val Val Ile Ala Thr Val Ile Val Ile Thr Leu Val MET Leu Lys Lys Lys Gln
 40                                           50

TAC ACA TCC ATT CAT CAT GGT GTG GAG GTT GAC GCC GCT GTC ACC CCA GAG
Tyr Thr Ser Ile His His Gly Val Glu Val Asp Ala Ala Val Thr Pro Glu
              60                                        70

GAG CGC CAC CTG TCC AAG ATG CAG CAG AAC GGC TAC GAA AAT CCA ACC TAC AAG
Glu Arg His Leu Ser Lys MET Gln Gln Asn Gly Tyr Glu Asn Pro Thr Tyr Lys
                               80                                    90

TTC TTT GAG CAG ATG CAG AAC TAG ACCCCCGCCA CAGCAGCCTC TGAAGTTGGA CAGCAAAACC
Phe Phe Glu Gln MET Gln Asn
                    99                                                    404
                        344        354        364        374        384        394
ATTGCTTCAC TACCCATCGG TGTCCATTTA TAGAATAATG TGGGAAGAAA CAAACCCGTT TTATGATTTA 474
   414        424        434        444        454        464
CTCATTATCG CCTTTTGACA GCTGTGCTGT AACACAAGTA AATGCCTGAA CTTGAATTAA TCCACACATC 544
   484        494        504        514        524        534
AGTAATGTAT TCTATCTCTC TTTACATTTT GGTCTCTATA CTACATTATT AATGGGTTTT GGTACTGTA
```

FIG. 4-2

```
         554        564        574        584        594        604        614
AAGAATTTAG CTGTATCAAA CTAGTGCATG AATAGATTCT CTCCTGATTA TTTATCACAT AGCCCCTTAG 624        634        644        654        664        674        684
CCAGTTGTAT ATTATTCTTG TGGTTTGTGA CCCAATTAAG TCCTACTTTA CATATGCTTT AAGAATCGAT 694        704        714        724        734        744        754
GGGGGATGCT TCATGTGAAC GTGGGAGTTC AGCTGCTTCT CTTGCCTAAG TATTCCTTTC CTGATCACTA 764        774        784        794        804        814        824
TGCATTTTAA AGTTAAACAT TTTTAAGTAT TTCAGATGCT TTAGAGAGAT TTTTTTTCCA TGACTGCATT 834        844        854        864        874        884        894
TTACTGTACA GATTGCTGCT TCTGCTATAT TTGTGATATA GGAATTAAGA GGATACACAC GTTTGTTTCT 904        914        924        934        944        954        964
TCGTGCCTGT TTTATGTGCA CACATTAGGC ATTGAGACTT CAAGCTTTTC TTTTTTTGTC CACGTATCTT 974        984        994       1004       1014       1024       1034
TGGGTCTTTG ATAAGAAAA GAATCCCTGT TCATTGTAAG CACTTTTACG GGGCGGGTGG GGAGGGGTGC 1044       1054
TCTGCTGGTC TTCAATTACC AAGAATTC
```

```
ATG GAT GCA GAA TTC CGA CAT GAC TCA GGA TAT GAA GTT CAT CAT
Met Asp Ala Glu Phe Arg His Asp Ser Gly Tyr Glu Val His His
 0                                         10

CAA AAA TTG GTG TTC TTT GCA GAA GAT GTG GGT TCA AAC AAA
Gln Lys Leu Val Phe Phe Ala Glu Asp Val Gly Ser Asn Lys
                 20

GGT GCA ATC ATT GGA CTC ATG GTG GGC GGT GTT GTC ATA GCG
Gly Ala Ile Ile Gly Leu Met Val Gly Gly Val Val Ile Ala
         30                                  40

ACA GTG ATC GTC ATC ACC TTG GTG ATG CTG AAC AAG AAA CAG
Thr Val Ile Val Ile Thr Leu Val Met Leu Lys Lys Lys Gln
                         50

TAC ACA TCC ATT CAT CAT GGT GTG GTG GAG GTT GAC GCC GCT
Tyr Thr Ser Ile His His Gly Val Val Glu Val Asp Ala Ala
                 60                                  70

GTC ACC CCA GAG GAG CGC CAC CTG TCC AAG ATG CAG CAG AAC
Val Thr Pro Glu Glu Arg His Leu Ser Lys Met Gln Gln Asn
                                 80

GGC TAC GAA AAT CCA ACC TAC AAG TTC TTT GAG CAG ATG CAG
Gly Tyr Glu Asn Pro Thr Tyr Lys Phe Phe Glu Gln Met Gln
                     90

AAC
Asn
```

```
GAA TTC GGA CAT GAT TCA GGA TTT GAA GTC CGC CAT CAA AAA CTG GTG TTC TTT
Glu Phe Gly His Asp Ser Gly Phe Glu Val Arg His Gln Lys Leu Val Phe Phe
 3                          10                          20
                              27                                     54

GCT GAA GAT GTG GGT TCG AAC AAA GGC GCC ATC ATC GGA CTC ATG GTG GGC GGC
Ala Glu Asp Val Gly Ser Asn Lys Gly Ala Ile Ile Gly Leu MET Val Gly Gly
                              81                  30                108

GTT GTC ATA GCA ACC GTG
Val Val Ile Ala Thr Val
             40
            135
```

FIG. 7-1   Nucleotide Comparison

```
W3  GAA TTC CGA CAT GAC TCA GGA TAT CAT CAT CAA AAA TTG GTG TTC TTT  54
               X                       X  XX              X
W9  GAA TTC GGA CAT GAT TCA GGA TTT GAA GTC CGC CAT CAA AAA CTG GTG TTC TTT  54

W3  GCA GAA GAT GTG GGT TCA AAC AAA GGT GCA ATC ATT GGA CTC ATG GTG GGC  108
      X                       X        X              X
W9  GCT GAA GAT GTG GGT TCG AAC AAA GGC GCC ATC ATC GGA CTC ATG GTG GGC  108

W3  GTT GTC ATA GCG ACA GTG  135
                  X   X
W9  GTT GTC ATA GCA ACC GTG  135
```

FIG. 7-2     Amino Acid Comparison

```
W3  Glu Phe Arg His Asp Ser Gly Tyr Glu Val His His Gln Lys Leu Val Phe Phe
                  X
W9  Glu Phe Gly His Asp Ser Gly Phe Glu Val Arg His Gln Lys Leu Val Phe Phe
                                      X

W3  Ala Glu Asp Val Gly Ser Asn Lys Gly Ala Ile Ile Gly Leu MET Val Gly Gly
W9  Ala Glu Asp Val Gly Ser Asn Lys Gly Ala Ile Ile Gly Leu MET Val Gly Gly

W3  Val Val Ile Ala Thr Val
W9  Val Val Ile Ala Thr Val
```

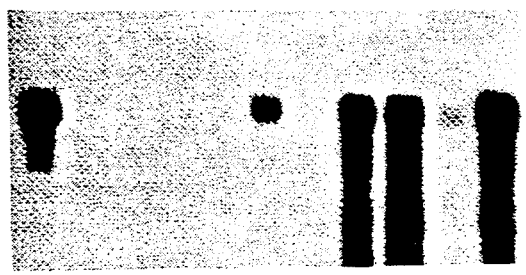
–28s FIG. 8A
Junction
–18s
–28s FIG. 8B
Insert
–18s
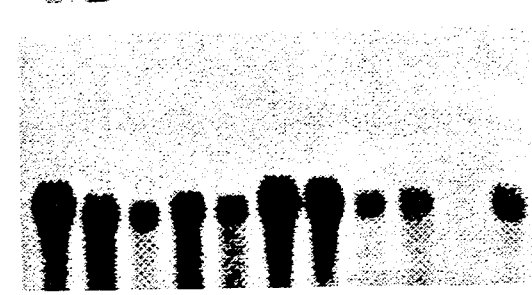
–28s FIG. 8C
Actin
–18s

FIG. 9A₁

```
    1                3                    5
 ┌──────────┬───────────────────┬──────────────────────┐
 CACCTGTCCAAGATGCAGCAGAACGGCTACGAAAATCCAACCTACAAGTTCTTTGAGCAGATGCAGAACTA
 GGCGGTGGACAGGTTCTACGTCGTCTTGCCGATGCTTTTAGGTTGGATGTTCAAGAAACTCTGCTACGTCTTGATTCGA
 └─────────────┴─────────────┬──────────────────────┘
 HaeII    2                4                6       HindII
```

FIG. 9C

NH2-Met-Thr-Ile-Thr-Leu-Thr-Thr-Thr-Thr-Thr-Thr- (beta-gal-thr leader).

655
Glu-Phe-Arg-His-Asp-Ser-Gly-Tyr-Glu-Val-His-His-Gln-Lys-Leu-Val-Phe-Phe-Ala-

Glu-Asp-Val-Gly-Ser-Asn-Lys-Gly-Ala-Ile-Ile-Gly-Leu-Met-Val-Gly-Gly-Val-Val-

Ile-Ala-Thr-Val-Ile-Val-Ile-Thr-Leu-Val-Met-Leu-Lys-Lys-Lys-Gln-Tyr-Thr-Ser-

Ile-His-His-Gly-Val-Val-Glu-Val-Asp-Ala-Ala-Val-Thr-Pro-Glu-Glu-Arg-His-Leu-

Ser-Lys-Met-Gln-Gln-Asn-Gly-Tyr-Glu-Asn-Pro-Thr-Tyr-Lys-Phe-Phe-Glu-Gln-Met-

751
Gln-Asn-COOH    (B-amyloid-related polypeptide)

FIG. 9D

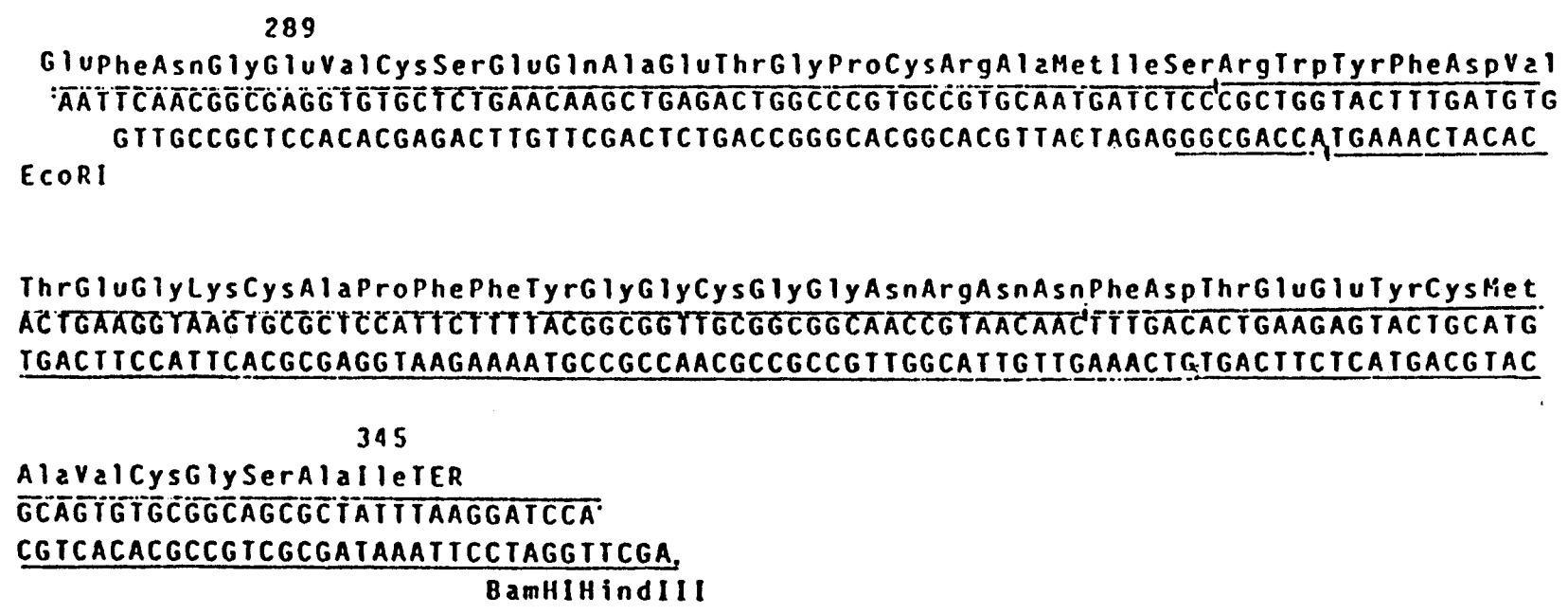

```
            289
GluPheAsnGlyGluValCysSerGluGlnAlaGluThrGlyProCysArgAlaMetIleSerGluArgTrpTyrPheAspVal
AATTCAACGGCGAGGTGTGTCTGAACAAGCTGAGACTGGCCCGTGCCGTGCAATGATCTCCGCTGGTACTTTGATGTG
        GTTGCCGCTCCACACGAGACTTGTTCGACTCTGACCGGGCACGTTACTAGAGGCGACCATGAAACTACAC
EcoRI

ThrGluGlyLysCysSerGlyPhePheTyrGlyGlyAsnArgAsnPheAspThrGluTyrCysMet
ACTGAAGGTAAGTGCGCTCTCCATTCTTTTACGGCCGGTTGCGGCGGCAACCGTAACACTTTGACACTGAAGAGTACTGCATG
TGACTTCCATTCACGCGAGGTAAGAAAATGCCGGCCAACGCCGCCGTTGGCATTGTTGAAACTGTGACTTCTCATGACGTAC
                345
AlaValCysGlySerAlaIleTER
GCAGTGTGCGGCAGCGCTATTTAAGGATCCA
CGTCACACGCCGTCGCGATAAATTCCTAGGTTCGA
                        BamHIHindIII
```

FIG. 13-1

TIHUBI : Inter-alpha-trypsin inhibitor (BPI type)
50.0% identity in 52 aa overlap

```
INSERT    1"  AVLPQEEGSGGQLVTEVTKKEDSCQLGYSAGPCMGMTSRYFYNGTSMACETFQYGGCM
                                                :::: :: :
TIHUBI    1'  EVCSEQAETGPCRAMISRWYFDVTEGKCAPFFYGGCGGGNRN
              :  .:   : ::::..: : :::: ::
INSERT   61"  GNGNNFVTEKECLQTCRTVAACNLPVIRGPCRAFIQLWAFDAVKGKCVLFPYGGCQGNGN

TIHUBI   42'  NFDTEEYCMAVCGSAI
              .: .: ...  ::
INSERT  121"  KFYSEKECREYCGVPGDEDEELL
```

TIBOBI : Inter-alpha-trypsin inhibitor (BPI type)
48.1% identity in 54 aa overlap

```
INSERT    1"                                                           EV
                                                                       ..
TIBOBI    1'  KADSCQLDYSQGPCLGLFKRYFYNGTSMACETFLYGGCGGNRNNFDTEEYCMAVCGSAI
INSERT    3"  CSEQAETGPCRAMISRWYFDVTEGKCAPFFYGGC              EYCMAVCGSAI
              :  :::::.: :  ::::::..:  :::: ::
TIBOBI   61'  CNLPIVQGPCRAFIQLWAFDAVKGKCVRFSYGGCKGNGNKFYSQKECKEYCGIPGEADER
INSERT   61"  CNLPVIRGPCRAFIQLWAFDAVKGKCVLFPYGGCQGNGNKFYSQKECKEYCGIPGEADER

TIBOBI  121'  LL
```

FIG. 13-2

TIBO : Basic protease inhibitor precursor - Bovine
47.4% identity in 57 aa overlap

```
                        EVCSEQAETGPCRAMISRWYFDVTEGKCAPFFYGGCGGNRNNFD
INSERT   1'             .:.. .:::.:.: :.......:  .:::: .:.::.
TIBO     1" PSLFNRDPPIPAAQRPDFCLEPPYTGPCKARIIRYFYNAKAGLCQTFVYGGCRAKRNNFK

45' TEEYCMAVCGSAI
             ..: :: .:.:.::
         61" SAEDCMRTCGGAIGPWGKTGGRAEGEGKG
```

TIBOR : Serum basic protease inhibitor - Bovine
42.9% identity in 56 aa overlap

```
                        EVCSEQAETGPCRAMISRWYFDVTEGKCAPFFYGGCGGNRNNFDTEEYCMAVCGSA
INSERT   1'             . :... .::::. . .:::::..  .:::: .:::...:  .:::. .:.:
TIBOR    1" TERPDFCLEPPYTGPCKAAMIRYFYNAKAGFCETFVYGGCRAKSNNFKSAEDCMRTCGGA

57' I
```

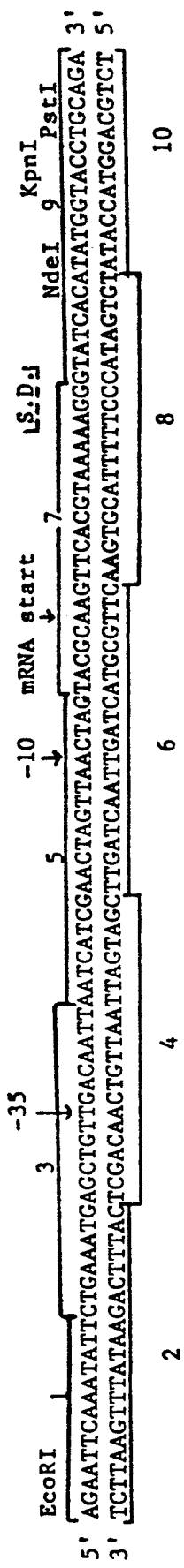
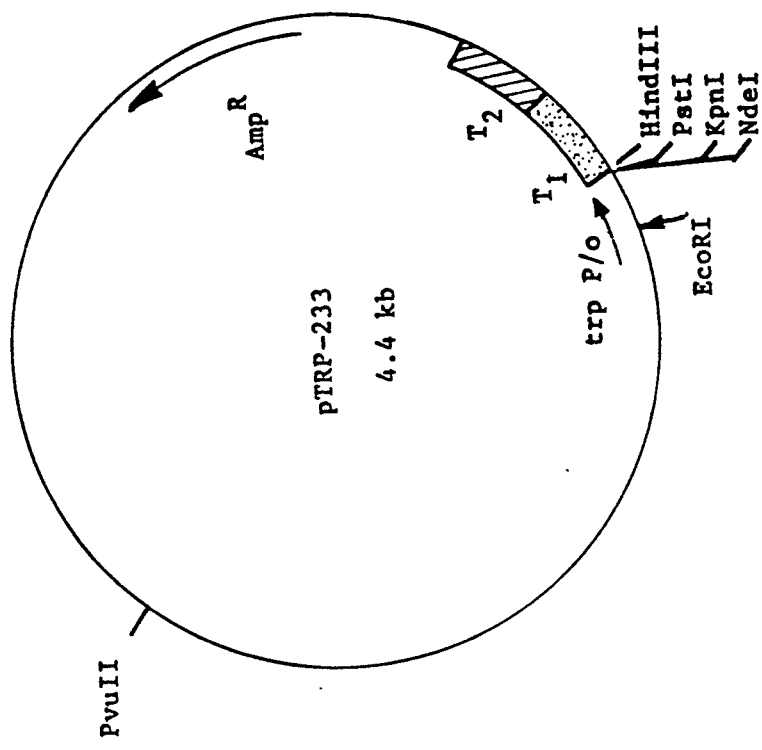
FIG. 14

CV-1 CELLS INFECTED
WITH A4₇₅₁-VACCINIA VIRUS
Western Blot

```
NdeI
TATG AAA AAG ACA GCT ATC GCG ATT GCA GTG GCA CTG GCT GGT TTC GCT ACC
 TAC TTT TTC TGT CGA TAG CGC TAA CGT CAC CGT GAC CGA CCA AAG CGA TGG
 Met Lys Lys Thr Ala Ile Ala Ile Ala Val Ala Leu Ala Gly Phe Ala Thr
                                    10

GTA GCG CAG GCC*GAG GTG TGC TCT GAA CAA GCT GAG ACT GGC CCG TGC CGT GCA
CAT CGC GTC CGG CTC CAC ACG AGA CTT GTT CGA CTC TGA CCG GGC ACG GCA CGT
Val Ala Gln Ala Glu Val*Cys Ser Glu Gln Ala Glu Thr Gly Pro Cys Arg Ala
         20                                        30

ATG ATC TCC*CGC TGG TAC TTT GAT GTG ACT GAA GGT AAG TGC GCT CCA TTC TTT
TAC TAG AGG GCG ACC ATG AAA CTA CAC TGA CTT CCA TTC ACG CGA GGT AAG AAA
Met Ile Ser Arg Trp*Tyr Phe Asp Val Thr Glu Gly Lys Cys Ala Pro Phe Phe
              40                              50

TAC GGC GGT TGC GGC GGC AAC CGT AAC AAC*TTT GAC ACT GAA GAG TAC TGC ATG
ATG CCG CCA ACG CCG CCG TTG GCA TTG TTG AAA CTG TGA CTT CTC ATG ACG TAC
Tyr Gly Gly Cys Gly Gly Asn Arg Asn Asn Phe Asp*Thr Glu Glu Tyr Cys Met
                        60                                        70

BamHI
GCA GTG TGC GGC AGC GCT ATT TAA GGATCCA
CGT CAC ACG CCG TCG CGA TAA ATT CCTAGGTTCGA         FIG.16A
Ala Val Cys Gly Ser Ala Ile        HindIII NdeI
TATG AAA CAA AGC ACT ATT GCA ATG GCA CTC TTA CCG TTA CTG TTT ACC CCT
 TAC TTT GTT TCG TGA TAA CGT TAC CGT GAG AAT GGC AAT GAC AAA TEG GGA
 Met Lys Gln Ser Thr Ile Ala Met Ala Leu Leu Pro Leu Leu Phe Thr Pro
                                    10

GTG ACA AAA GCC*GAG GTG TGC TCT GAA CAA GCT GAG ACT GGC CCG TGC CGT GCA
CAC TGT TTT CGG CTC CAC ACG AGA CTT GTT CGA CTC TGA CCG GGC ACG GCA CGT
Val Thr Lys Ala Glu Val*Cys Ser Glu Gln Ala Glu Thr Gly Pro Cys Arg Ala
         20                                        30

ATG ATC TCC*CGC TGG TAC TTT GAT GTG ACT GAA GGT AAG TGC GCT CCA TTC TTT
TAC TAG AGG GCG ACC ATG AAA CTA CAC TGA CTT CCA TTC ACG CGA GGT AAG AAA
Met Ile Ser Arg Trp*Tyr Phe Asp Val Thr Glu Gly Lys Cys Ala Pro Phe Phe
              40                              50

TAC GGC GGT TGC GGC GGC AAC CGT AAC AAC*TTT GAC ACT GAA GAG TAC TGC ATG
ATG CCG CCA ACG CCG CCG TTG GCA TTG TTG AAA CTG TGA CTT CTC ATG ACG TAC
Tyr Gly Gly Cys Gly Gly Asn Arg Asn Asn Phe Asp*Thr Glu Glu Tyr Cys Met
                        60                                        70

BamHI
GCA GTG TGC GGC AGC GCT ATT TAA GGATCCA
CGT CAC ACG CCG TCG CGA TAA ATT CCTAGGTTCGA         FIG.16B
Ala Val Cys Gly Ser Ala Ile        HindIII
```

METHODS OF TREATMENT USING ALZHEIMER'S AMYLOID POLYPEPTIDE DERIVATIVES

CROSS-REFERENCE TO RELATED APPLICATIONS

This is a continuation-in-part of U.S. Ser. No. 361,912, filed Jun. 6, 1989, which is a continuation of U.S. Ser. No. 359,911, filed May 12, 1989 (abandoned), which is the U.S. National Stage application of PCT W088/03951, filed Nov. 12, 1987, which is a continuation-in-part of U.S. Ser. No. 087,002, filed Aug. 18, 1987 (abandoned), which is a continuation-in-part of U.S. Ser. No. 008,810, filed Jan. 30, 1987 (abandoned), which is a continuation-in-part of U.S. Ser. No. 948,376, filed Dec. 31, 1986 (abandoned), which is a continuation-in-part of U.S. Ser. No. 932,193, filed Nov. 17, 1986 (abandoned) each of the above-referred to applications is incorporated herein by reference and priority is claimed to these applications under 35 USC Section 120.

FIELD OF THE INVENTION

The invention generally relates to the field of pharmaceutical compositions and methods of using such compositions in order to treat a variety of diseases. More specifically, the invention relates to pharmaceutical compositions containing the A4i protease and to analogs of that protease to treat diseases associated with Kunitz-type basic protease inhibitors.

BACKGROUND ART

The demography of Alzheimer's disease is becoming progressively better understood. It is estimated that over 5% of the U.S. population over 65 and over 15% of the U.S. population over 85 are beset with this disease (Cross, A.J., *Eur J Pharmacol* (1982) 82:77-80; Terry, R.D., et al., *Ann Neurol* (1983) 14:497506). It is believed that the principal cause for confinement of the elderly in long term care facilities is due to this disease, and approximately 65% of those dying in skilled nursing facilities suffer from it.

To confound the problem that therapy is at present a matter of experimentation, diagnosis is also unreliable. There is no straightforward diagnostic test, and diagnosis is made by a series of evaluations based on negative results for alternative explanations for the symptomologies exhibited. Assuming that the presence of the disease can be assessed accurately after death by autopsies of the brain, current results show that present diagnostic methods among living individuals carry an approximately 20% rate of false positives.

It would be extremely helpful in effecting appropriate care for patients and in developing therapies to have a straightforward assay method for diagnosing the presence of Alzheimer's disease. The invention described below provides an approach to this diagnosis.

Certain facts about the biochemical and metabolic phenomena associated with the presence of Alzheimer's disease are known. Two morphological and histopathological changes noted in Alzheimer's disease brains are neurofibrillary tangles (NFT) and amyloid deposits. Intraneuronal neurofibrillary tangles are present in other degenerative diseases as well, but the presence of amyloid deposits both in the interneuronal spaces (neuritic plaques) and in the surrounding microvasculature (vascular plaques) seems to be characteristic of Alzheimer's. Of these, the neuritic plaques seem to be the most prevalent (Price, D.L., et al., *Drug Development Research* (1985) 5:59-68). Plaques are also seen in the brains of aged Down's Syndrome patients who develop Alzheimer's disease.

The protein which makes up the bulk of these plaques has been partially purified and sequenced. plaquerich brains of deceased Alzheimer's patients have been used as a source to extract an approximately 4.2 kd "core" polypeptide, amyloid plaque core protein (APCP), herein referred to as "β-amyloid core protein." This peptide was designated β-protein by Glenner, G., et al., [*Biochem Biophys Res Commun* (1984) 120:885-890]. The amino acid sequence of the amino-terminus has been determined [Glenner, G., et al., *Biochem Biophys Res Commun* (1984) 122:1131-1135; Masters, C.L., et al., *Proc Natl Acad Sci USA* (1985) 82:1245-4259] and the amino acid sequences reported by the two groups are identical except that Glenner et al. report a glutamine at position 11 for Alzheimer Disease cerebral vascular amyloid whereas Masters et al. report glutamic acid at position 11. Also, the former authors report that the cerebral vascular amyloid has a unique amino-terminus while the latter authors report that the form found in amyloid plaque cores has a "ragged" amino-terminus—i.e., peptides isolated from this source appear to be missing 3, 7, or 8 amino acids from the amino-terminus. Both groups have shown that the same peptide is found in the amyloid plaque cores and vascular amyloid of adult Down's syndrome-afflicted individuals and report glutamic acid at position 11.

Further studies on the β-amyloid core protein were also conducted by Roher, A., et al., *Proc Natl Acad Sci USA* (1986) 83:2662-2666 which showed the complete amino acid composition of the protein, and verified that it matched that of no known protein. The compositions obtained were, however, evidently not in agreement with those of Allsop, D., et al., *Brain Res* (1983) 259:348-352; nor were they in agreement with those published by Glenner or Masters (supra).

Wong, C.W., et al., *Proc Natl Acad Sci USA* (1985) 82:8729-8732 showed that a synthetic peptide which was homologous to the first ten amino acids of the β-amyloid core protein described by Masters (supra) was able to raise antibodies in mice and that these antibodies could be used to stain not only amyloid-laden cerebral vessels, but neuritic plaques as well. These results were confirmed by Allsop, D. et al., *Neuroscience Letters* (1986) 68:252-256 using monoclonal antibodies directed against a synthetic peptide corresponding to amino acids 8-17. Thus, in general, the plaque protein found in various locations of the brain of Alzheimer's patients appears to be similar in immunoreactivity. It is highly insoluble, as shown by the inability to achieve solubilization in many commonly used denaturants such as detergents and chaotropic agents (Masters, supra, Allsop, D., et al., (supra)).

It is believed, by analogy to some other amyloid proteins, that β-amyloid core protein may be formed from a precursor in the peripheral circulatory system or lymphatic system. There are six known instances of disease-associated amyloid deposits in which the nature of the precursor protein for the amyloid protein is known: for primary amyloidosis, the source is an immunoglobulin light chain; for secondary amyloidosis, the precursor is amyloid A protein; for familial amyloid polyneuropathy and senile cardiac amyloidosis, prealbumin or a variant thereof; for medullary carcinoma of thyroid, a procalcitonin fragment; and for hereditary cerebral hemorrhage, gamma-trace fragment (See, e.g., Glenner, G. *New England Journal of Medicine* (1980) 302:1283; Sletton, K., et al., *Biochem J* (1981) 195:561; Benditt, et al., *FEBS Lett* (1971) 19:169; Sletton, K., et al., *Eur J Biochem* (1974) 41:117; Sletton, K., et al., *J Exp Med* (1976) 143:993). The foregoing is a partial list and there are at least a number of additional references with regard to procalcitonin fragment as a precursor for the amyloid of the thyroid carcinoma. Alternatively, or additionally, such a precursor for β-amyloid core protein may be produced in the brain.

It has been described that a protein containing the β-amyloid core protein sequence within the framework of a larger protein exists (Kang, J., et al., *Nature* (1987) 325:733-736). This protein, which is a potential precursor in vivo to the β-amyloid core protein, was predicted from the sequence of a cDNA clone isolated from a human fetal brain tissue cDNA library and consists of 695 amino acid residues wherein the amino terminus of the β-amyloid core protein begins at position 597. By analogy to the above described series, it may be that such a precursor or a fragment thereof circulates in the serum at a level differentiable in Alzheimer's victims relative to unafflicted individuals. Alternatively or additionally, such differences may be detected in the cerebral spinal fluid.

Since the discovery of the novel precursor protein described in the present invention, others have characterized similar amyloid precursor proteins (Kitaguchi et al., *Nature* 331:530-532 (1988)) or a slightly larger, 770 amino acid amyloid precursor (Tanzi et al., *Nature* 331:528-530 (1988)), all of which contain an approximately 57 amino acid insert. This particular insert sequence is highly homologous to a number of Kunitz-type inhibitors which are specific for a number of serine proteases.

SUMMARY OF THE INVENTION

Pharmaceutical compositions containing a 57 amino acid protease inhibitor and uses for those compositions are taught. The protease inibitor is referred to as A4i which is associated with Alzheimer's disease. In addition to the A4i protease, other analogs are taught as are pharmaceutical compositions containing such analogs and their uses in treating a variety of abnormalities associated with Kunitz-type basic protease inhibitors. For example, it has been found that pharmaceutical compositions containing A4i protease and analogs thereof inhibit plasmin and tryptase, and also inhibit pancreatic trypsin, alpha-chymotrypsin, tissue kallikrein and serum kallikrein. Certain diseases are associated with a general release of proteases such as trypsin, chymotrypsin and elastase into the circulatory system. Accordingly, pharmaceutical compositions containing A4i and analogs which inhibit the action of these proteases can be used in the management of such diseases.

An important object of the present invention is to provide an approved method for treating diseases associated with the release of proteases which involves administering to a patient suffering from such diseases a pharmaceutically effective amount of a protein (or analog thereof) having the following amino acid sequence:

GluValCysSerGluGlnAlaGluThrGlyProCysArgAlaMet
IleSerArgTrpTyrPheAspValThrGluGlyLysCysAla
ProPhePheTyrGlyGlyCysGlyGlyAsnArgAsnAsnPhe

-continued
AspThrGluGluTyrCysMetAlaValCysGlySerAlaIle.

Yet another important object of the present invention is to provide pharmaceutical compositions comprised of pharmaceutically acceptable carriers and excipient materials in combination with the above-referred to protein.

Yet another important object of the present invention is to disclose and describe pharmaceutically acceptable compositions having fibrilolytic inhibitory activity which compositions are comprised of a pharmaceutically acceptable carrier and excipient materials along with a fibrilolytically inhibitory effective amount of the above-referred to protein.

Another important object of the present invention is to provide pharmaceutical compositions and methods for using those compositions which are helpful in inactivating fibrin dissolution at a wound sight on a subject and thus promoting wound repair.

Another object of the present invention is to provide pharmaceutical compositions having thrombolytic activity which compositions are comprised of thrombolytically effective amounts of the above-referred to protein in combination with pharmaceutically acceptable excipient materials.

Important features of the present invention are that the pharmaceutical compositions of the invention are useful in inhibiting a wide range of biochemical reactions associated with diseases.

An advantage of the present invention is that the proteins used in the compositions of the invention are not toxic and do not cause undesirable side effects.

These and other objects, advantages and features of the present invention will become apparent to those persons skilled in the art upon reading the details of the structure, synthesis, formulation and usage as more fully set forth below, reference being made to the accompanying figures, DNA and amino acid sequences forming a part hereof.

BRIEF DESCRIPTION OF THE DRAWINGS

FIG. 1, parts 1-4 shows the base sequence of a cDNA clone, designated λAPCP168i4, which encodes amino acids 1-751 of β-amyloid-related protein. The 168 bp insert, which distinguishes this clone from the Kang et al. sequence, is underlined.

FIG. 2 shows a DNA sequence of a genomic clone encoding the first 18 amino acids of the β-amyloid core protein as described by Masters et al. It also encodes, immediately preceding these amino acids, a methionine codon which could potentially be used as an initiating codon;

FIG. 3, parts 1 and 2, shows the base sequence of a cDNA clone, designated λSM2W4, whose 3' end encodes the first four amino acids of β-amyloid core protein. It also encodes, immediately preceding these amino acids, a methionine codon as described above;

FIG. 4, parts 1 and 2, shows the base sequence of a cDNA clone, designated λSM2W3, which encodes 97 amino acids; the first 26 of these correspond to the region of the β-amyloid core protein described by Masters et al., from $Glu_3$ through $Ala_{28}$;

FIG. 5 shows the base sequence and corresponding amino acid sequence of a β-amyloid-related protein deduced from λSM2W4 and λSM2W3;

FIG. 6 shows the nucleotide and deduced amino acid sequence of the λSM2W9 β-amyloid clone;

FIG. 7, parts 1 and 2, shows a comparison of the sequences of λSM2W3 and λSM2W9;

FIG. 8 (A,B,C) shows the detection of mRNAs for λAPCP168i4 and the mRNA described by Kang et al. on a Northern blot produced using RNA's isolated from human brain and human cells in culture and hybridized to oligonucleotide probes which are specific for each species;

FIG. 13, parts 1 and 2, shows the relatedness of the peptide encoded by the λAPCP168i4 168 bp insert to a superfamily of proteins many of whose members exhibit inhibitory activity for basic proteases; and FIG. 14 shows the construction of a synthetic tryptophan operon promoter and operator regulatory sequence, and a restriction site map of plasmid pTRP233.

FIG. 16 is an illustration of the oligonucleotide sequences used to construct chimeric genes containing either the ompA signal sequence fused to the protease inhibitor sequence (FIG. 16A) or the phoA signal sequence fused to the protease inhibitor sequence (FIG. 16B). The asterisks indicate the individual oligonucleotides used for each construction.

DETAILED DESCRIPTION OF THE INVENTION

Figure 9B:
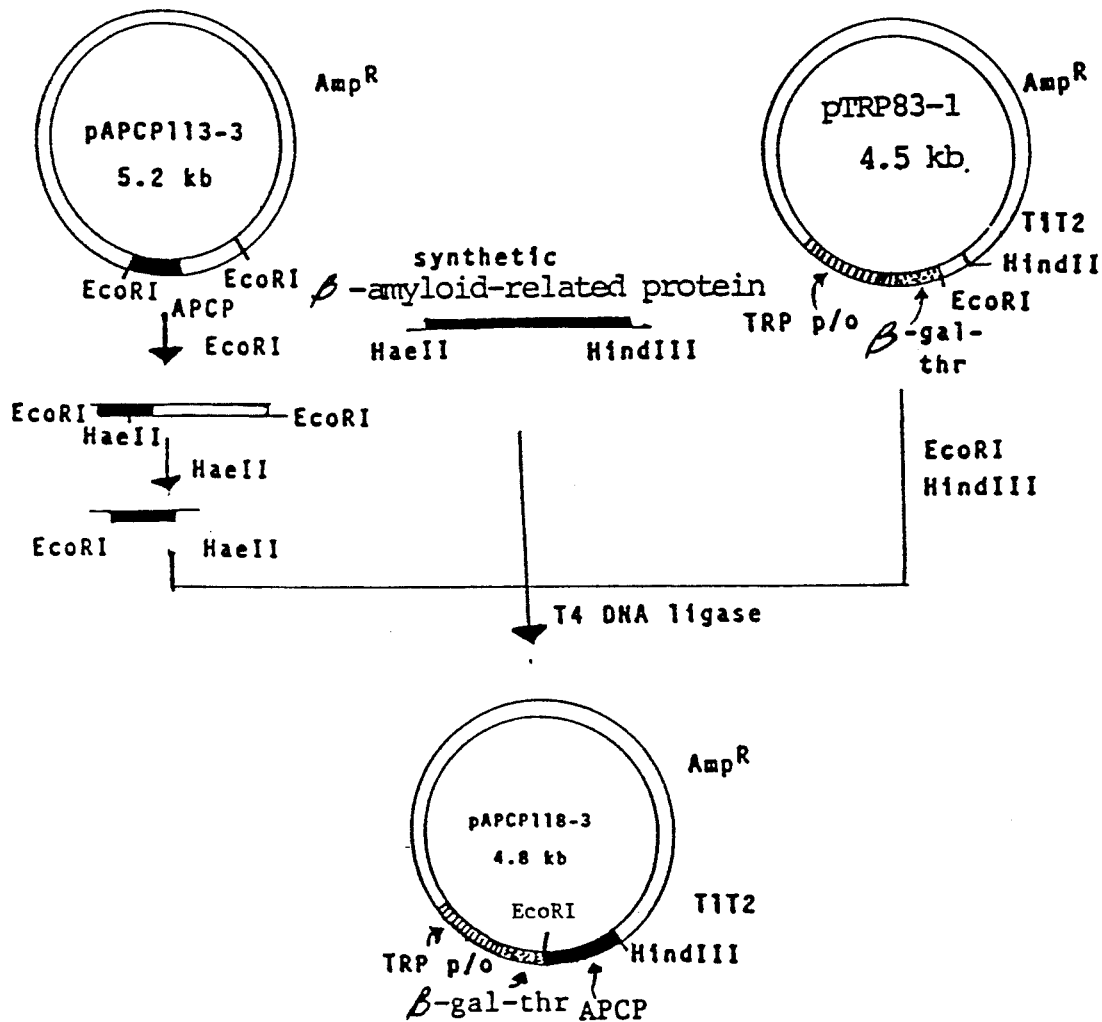
FIG. 9 (A,B,C,D) shows the construction scheme for a bacterial expression vector for the production of a β-amyloid-related protein in bacteria.

Before the present pharmaceutical compositions containing protease inhibitors and analogs thereof and methods of using same are described, it is to be understood that this invention is not limited to the particular formulations or uses described as such formulations and uses may, of course, vary. It is also to be understood that the terminology used herein is for purposes of describing particular embodiments only, and it not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a protease inhibitor" includes mixtures of such protease inhibitors, reference to "an analog of an inhibitor" includes mixtures of such analogs and reference to "the method of use" includes a plurality of such methods of the type known to those skilled in the art or which will become apparent to those skilled in the art upon reading this disclosure.

A. Definitions

As used herein, "β-amyloid core protein" means the protein described by Masters, C.L., et al., *Proc Natl Acad Sci USA* (1985) 82:4245–4249, herein referred to as "Masters, et al". This approximately 4 kD protein is defined at the amino terminus by sequence analysis as a mixture of four peptides with slightly different amino termini, the amino termini of the three smaller peptides being completely encoded by that of the largest. The first 28 amino acids of the longest form is $Asp_1-Ala_2-Glu_3-Phe_4-Arg_5-His_6-Asp_7-Ser_8-Gly_9-Tyr_{10}$
$Glu_{11}-Val_{12}-His_{13}-His_{14}-Gln_{15}-Lys_{16}-Leu_{17}-Val_{18}-Phe_{19}$
$Phe_{20}-Ala_{21}-Glu_{22}-Asp_{23}-Val_{24}-Gly_{25}-Ser_{26}-Ser_{27}-Ala_{28}$.

"β-amyloid-related protein" or "β-amyloid-related peptide" are defined herein as those proteins containing within their sequence the β-amyloid core protein sequence defined above or fragments of such proteins which do not necessarily include the β-amyloid core protein sequence as defined above. As an example, this term is used to refer to the protein described by Kang, J., et al., *Nature* (1987) 325:733–736, herein referred to as "Kang et al.", which contains the β-amyloid core protein within its structure at amino acid 597 of a 695 amino acid protein. As another example, it refers to the protein encoded by λAPCP168i4, shown in FIG. 1, which, within its structure, contains the β-amyloid core protein at amino acid 653 of a 751 amino acid protein.

"Immunogenic β-amyloid core peptide" or "immunogenic β-amyloid-related peptide" refer to peptides whose amino acid sequences match those of some region of the β-amyloid core protein or β-amyloid-related protein, and which are capable of provoking an antibody response in an immunized animal.

"Genetic predisposition to Alzheimer's disease" refers to an identifiable genetic mutation or alteration found in the genomes of individual's with Alzheimer's disease, or those individuals destined to develop Alzheimer's disease, but not normal (nondiseased) individuals.

"A4i" as used herein refers to a polypeptide corresponding to the novel serine protease inhibitor encoded by the polynucleotide derived from the bacteriophage λAPCP168i4. The A4i polypeptide is not necessarily physically derived from the expression product of this bacteriophage, but may be generated in any manner, including peptide synthesis, recombinant DNA techniques or a combination thereof. "Corresponding" means homologous to or substantially equivalent to the designated sequence.

B. DNA Sequences

DNAs corresponding to β-amyloid core protein or β-amyloid-related protein sequences are useful as probes in diagnosis. Several DNAs containing sequences encoding portions of β-amyloid-related protein sequence, and β-amyloid core protein sequence with adjacent noncoding segments are disclosed herein. These DNA sequences in whole or in part, are thus useful in diagnosis, either as intact probes, or as fragments In particular, the invention includes a DNA sequence which encodes a β-amyloid-related protein comprising the nucleotide sequence and corresponding, deduced amino acid sequence set forth in FIG. 1. This DNA sequence encodes an approximately 82,610 dalton protein containing the β-amyloid-related core protein.

The present β-amyloid protein cDNA sequence, set forth in FIG. 1, can be isolated from bacteriophage λAPCP168i4. This human fibroblast cDNA clone was obtained from a cDNA library prepared in λgt10 using standard techniques from SV40-transformed fibroblast (SV80) cells (Todaro, G.J., et al., Science (1966) 153:1252-1-254). The λgt10-SV80 library was screened with a mixture of labelled oligonucleotides. Two unique phage containing β-amyloid-related sequences were obtained; these β-amyloid-related sequences were subcloned into a plasmid vector and sequencing analysis revealed a sequence co-linear with the sequence encoding the Kang et al. β-amyloid-related protein, except for the presence of a 168 basepair insert. The 168 basepair insert interrupts the codon for Val$_{289}$ of the Kang et al. sequence, resulting in the loss of this amino acid from the λAPCP168i4 protein. The 168 basepair insert, together with the 3 basepairs gained from the interrupted Val$_{289}$ codon, encode 57 new amino acids, which are underlined in FIG. 1. Downstream of this insertion, at codon 653 of FIG. 1, lies the amino-terminal aspartate of the β-amyloid core protein described by Masters et al. The λAPCP168i4 clone was deposited at ATCC on Jul. 1, 1987 under the accession number 40347.

Particularly useful are those sequences which encode the 57 amino acid insert found in λAPCP168i4, as well as sequences encoding the corresponding "junction" of the Kang et al. β-amyloid-related protein sequence.

For example, one preferred embodiment comprises DNA sequences encoding a β-amyloid-related protein having an amino acid sequence corresponding to residues 289 through 345 of the above-identified protein. Thus, this embodiment comprises a β-amyloid-related protein of the amino acid sequence:

Glu Val Cys Ser Glu Gln Ala Glu Thr Gly Pro Cys Arg Ala
10

Met Ile Ser Arg Trp Tyr Phe Asp Val Thr Glu Gly Lys Cys
20

Ala Pro Phe Phe Tyr Gly Gly Cys Gly Gly Asn Arg Asn Asn
30                                              40

Phe Asp Thr Glu Glu Tyr Cys Met Ala Val Cys Gly Ser Ala
50

Ile.

This particular peptide, including any fragments thereof, distinguishes the present β-amyloid-related protein from other reported forms.

In another preferred embodiment, the invention discloses a β-amyloid-related protein having the DNA sequence and deduced amino acid sequence corresponding to amino acid residues 284-Val$_{289}$-(∇289–345)-349 of the β-amyloid-related sequence set forth in FIG. 1 (wherein ∇ symbolizes a deletion of residues 289through 345). An oligopeptide spanning this specific region would be useful to generate a protein specific diagnostic reagent to differentiate between the β-amyloid-related protein genetic variant described by Kang et al. and the β-amyloid-related protein of the present invention. Thus, this embodiment comprises a β-amyloid-related protein of the amino acid sequence:

Glu Glu Val Val Arg Val Pro Thr Thr Ala

A smaller peptide contained within the sequence of this peptide might also be used.

Oligonucleotides specific for the 168 basepair insert and for the junctions of this region of the β-amyloid-related protein described by Kang et al. can be synthesized and used to compare the levels of mRNA expression of these two distinct proteins. As an example, oligonucleotides specific for the 168 basepair insert, designated oligo #2734:

```
        10          20          30          40          50
(CGCCGTAAAA GA''T''GGGC.. CACTTCCCTT CAGTCACATC AAAGTACCAG
         60
CGGGAGATCA)
``` and for the "junction" region, designated oligo #2733:

```
     10          20          30
(CTGCTGTTGT AGGAACTCGA ACCACCTCTT)
``` were synthesized using phosphoramidite chemistry on an Applied Biosystems DNA synthesizer.

The "junction" oligo is complementary to 15 basepairs on either side of the insert and is used to distinguish between the published β-amyloid-related protein sequences and the λAPCP168i4 sequences by specific hybridization conditions known in the art under which a 15 basepair perfect match is unstable, while a 30 basepair perfect match is stable. These oligonucleotides are used to screen cDNA libraries or mRNA from various sources as an assay for measuring the level of expression of a specific sequence.

Another example, described below, is a genomic sequence encoding the first 18 amino acids (19 if Met is included) of the β-amyloid protein sequence characteristic of Alzheimer's disease in neuritic plaques. The clone was obtained in λ Charon 4A from the genomic library described by Lawn, R.M., et al., Cell (1978) 15:1157-1174 and has been partially sequenced, as shown in FIG. 2. As seen, the sequenced portion of the genomic clone includes a 57 base pair segment which encodes the amino acids 1-18 of the previously reported β-amyloid core protein and a methionine immediately preceding. Downstream of the amino acid 18 codon, the genomic sequence diverges in codon sequence from that expected from the reported amino acid sequence of β-amyloid core protein. By reference to the protein encoded by the sequence of FIG. 4, and by inspection of the sequences flanking this region using knowledge known in the art, this divergence is likely to be an intron sequence This clone, designated λSM2, was deposited at ATCC on Nov. 13, 1986.

A HindIII/RsaI probe derived from the genomic clone (see FIG. 2) was used as a probe to isolate, according to standard procedures, cDNA fragments from a cDNA library constructed in λgt10 from temporal and parietal cortical tissue of a normal human brain (the individual was a 55 year old man who died of myocardial infarction). The three cDNA clones which were isolated were sequenced conventionally, and matched with amino acid sequences in each of the three possible reading frames to identify regions coding for β-amyloid-related proteins One of the clones, designated λSM2W4, contains a 3'-end terminal sequence which encodes the Asp Ala Glu Phe amino acids at the 5'-end of β-amyloid-core protein, as seen in FIG. 3, which shows the complete base sequence of the clone. The Asp1 codon is immediately preceded by a methionine codon. A second clone, designated λSM2W3, contains a 5' region segment which has a 6 bp overlap with the 3' end of the λSM2W4 clone (an EcoRI restriction site), encoding amino acids 3 and 4 of the β-amyloid core protein, and an additional 95 codons which encode the remainder of a β-amyloid-related protein. The DNA sequence for the 100 amino acid protein (including Met) encoded in λSM2W4 and λSM2W3 is shown in FIG. 5. It is, of course, understood that the methionine is probably processed in vivo, and that the β-amyloid-related protein represented in this figure may thus be a 99 amino acid sequence.

A third cDNA clone encodes a portion of a β-amyloid-related protein which differs from λSM2W3 in the region shown by 15 nucleotide differences and 4 amino acid differences in the region of amino acids 3–44 of FIG. 5. The DNA sequence and deduced amino acid sequence for this clone, designated λSM2W9 are given in FIG. 6. A comparison with λSM2W3 is given in FIG. 7.

C. Protein Production

The cDNA clones described herein permit construction of coding sequences which may be expressed to obtain a complete β-amyloid-related protein, an 100 amino acid β-amyloid-related protein containing the amino-terminal sequences reported for β-amyloid core protein, and other desired proteins. These sequences can be inserted in a suitable expression vector for production of protein. Details of the method of constructing a DNA subsequence of FIG. 1 and insertion of this sequence into a bacterial expression vector is provided in Example 2.

Briefly, an E. coli expression vector, designated pAPCP118-3, was constructed for the expression of a fusion protein consisting of amino acid residues 655 to 751 set forth in FIG. 1. The construction of pApCP1-18-3 was accomplished by joining the following three fragments: (1) a plasmid backbone (consisting of pBR322 replication functions, an ampicillin resistance gene, the tryptophan promoter and operator, a ribosome binding site, DNA encoding the seven amino terminal codons of the␤-galactosidase structural gene followed by six threonine residues, and transcription termination signals); (2) an EcoRI-HaeII fragment encoding amino acid residues 655–728 of the FIG. 1 sequence; and (3) a synthetic fragment encoding amino acid residues 729–751 of the FIG. 1 sequence, followed by a stop codon.

The resulting vector was used to transform E. coli W3110 and expression of the fusion protein was induced by reducing the tryptophan concentration followed by the addition of 3-β-indoleacrylic acid. The resulting protein can be purified using conventional purification techniques and the resulting purified material is available for use in the production of antibodies for diagnostic assays.

Figure 10:
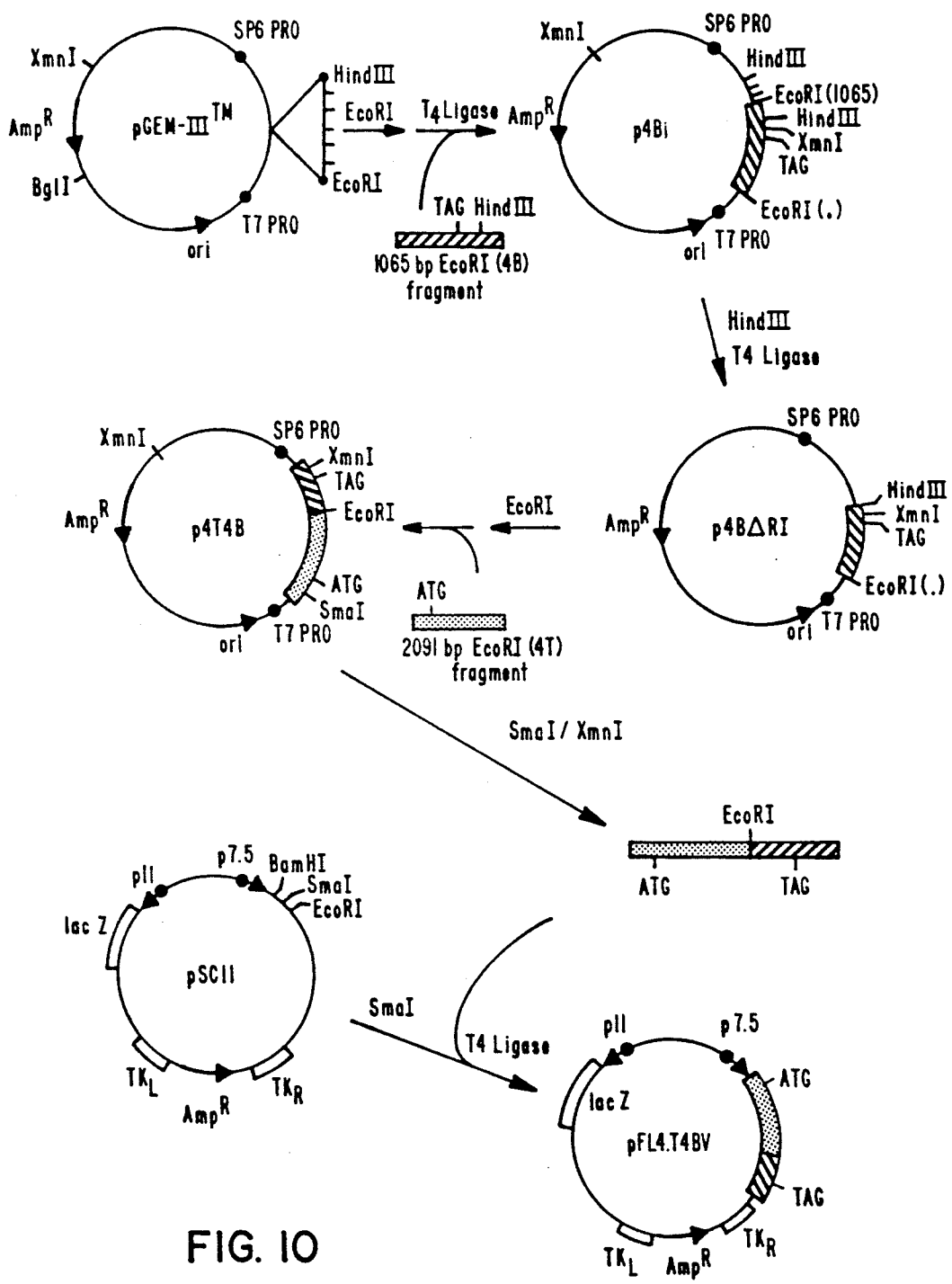
FIG. 10 shows the construction scheme for a recombinant vaccinia virus expression vector for the expression of the protein encoded by λAPCP168i4.
Figure 11:
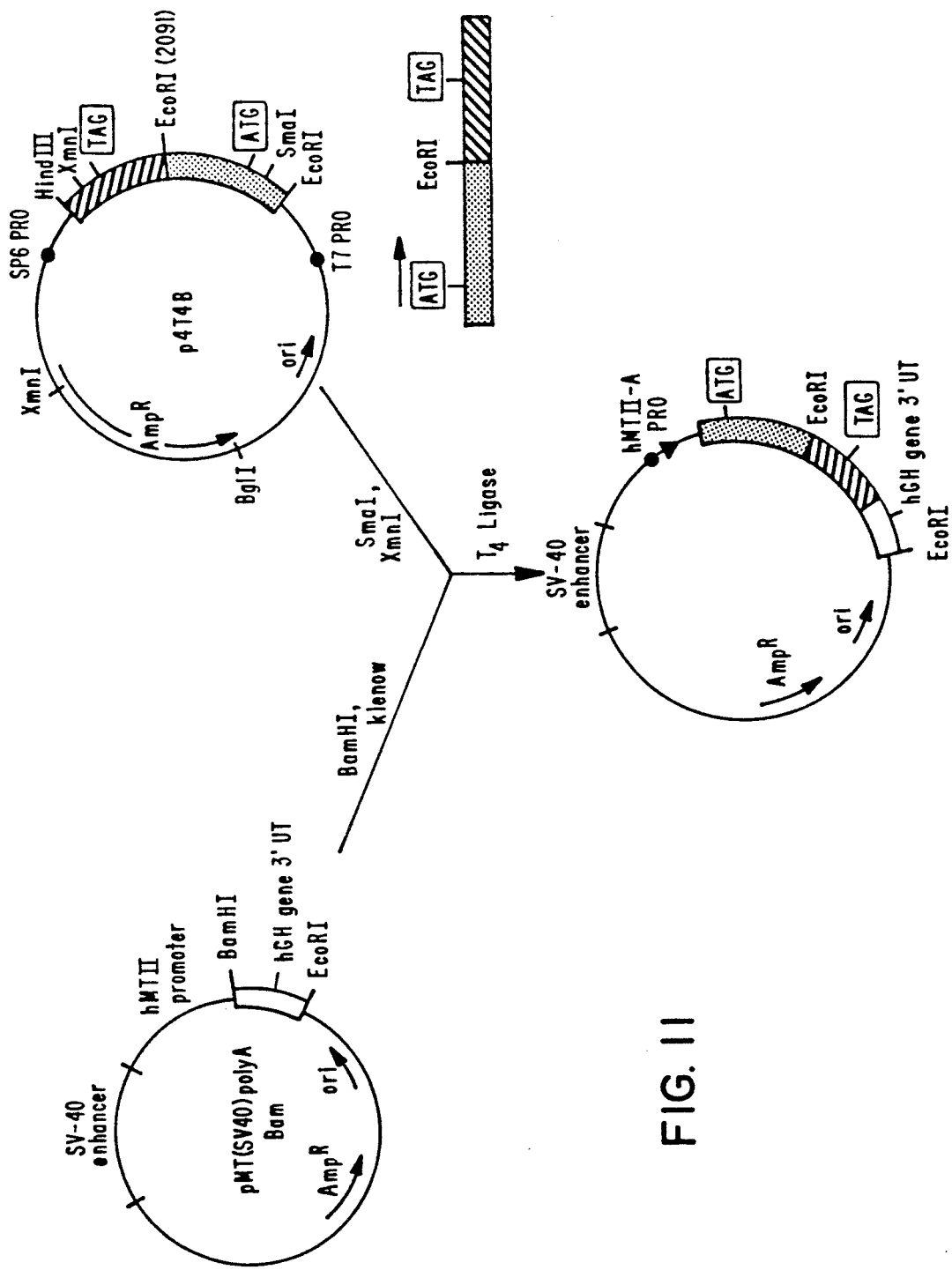
FIG. 11 shows the construction scheme for a mammalian cell expression vector for the expression of the protein encoded by λAPCP168i4.

The complete coding sequence of the β-amyloid-related protein set forth in FIG. 1 was subcloned in two fragments from the deposited λAPCP168i4 clone and inserted into pSCll, a vaccinia virus expression vector. The construction of the resulting vector, pFL4T4BV, is illustrated in FIG. 10. Briefly, an approximately 1.06 kilobase (kb) EcoRI fragment, spanning amino acid residues 655–751 of the protein illustrated in FIG. 1, was cloned into EcoRI-digested plasmid pGEM-3 TM (available from Promega Biotec) to create an intermediate vector designated p4BI. Subsequently p4BI was digested with HindIII to remove much of the 3'-non-coding sequence of the β-amyloid-related sequence. The resulting vector p4B∇RI was digested with EcoRI and treated with calf intestinal alkaline phosphatase prior to ligation to the 2088 bp EcoRI fragment derived from λAPCP168i4 to form p4T4B. This plasmid was digested with SmaI and XmnI to generate a 2678 bp fragment spanning the complete protein encoding sequence set forth in FIG. 1.

The gene encoded by this SmaI-XmnI fragment was inserted into a well-known vaccinia viral vector, pSCll, for subsequent expression of the β-amyloid-related protein in CV-1 monkey kidney cells using a eucaryotic transient expression system as described by Cochran, M.A., et al., Proc Natl Acad Sci USA (1985) 82:19–23. More commonly, this vector is used for in vivo protein and antibody production in animals after its sequences have been inserted into the vaccinia virus genome (see "Antibody Production" section below).

Similarly, mammalian vectors can be utilized for expression of the β-amyloid core protein or β-amyloid-related proteins described herein. For example, plasmid phGH-SV (10) (a plasmid described in EPA 217,822, published Apr. 15, 1987, and incorporated herein by reference) contains a pUC8 plasmid backbone, hMT-IIa gene promoter and regulator elements, SV-40 DNA promoter and enhancer elements, and the coding portions of the hGH gene and 3' regulatory sequences. This plasmid can be digested with BamHI and SmaI and treated with BamHI linkers to delete the human growth hormone protein encoding sequence and leaving the 3'-noncoding sequences and regulatory elements attached to the plasmid backbone. This approximately 5100 base pair DNA piece is gel purified and ligated to BamHI linkers. Digestion with BamHI, repurification of the DNA fragment and subsequent ligation result in a plasmid designated pMTSV40 polyA Bam which contains the structural and regulatory elements comprising a mammalian cell expression vector. After BamHI digestion of pMTSV40 polyA BamHI and repair in the presence of DNA polymerase I and all four dNTPs, this vector is available for insertion of the ~2678 bp SmaI-XmnI restriction fragment of plasmid p4T4B. The resulting vector can then be used for efficient protein expression in CHO cells as described in Example 4.

In addition, the sequence information from the λSM2W4 clone, illustrated in FIG. 3, combined with the sequences present in the λSM2W3 clone, may be used to construct a mammalian cell expression vector encoding the protein described in FIG. 5.

The secreted protease inhibitor may be recovered in a biologically active, refolded and substantially pure form from the bacterial broth using a solid support affinity matrix, such as, for example, Sepharose beads, to which a serine protease with high affinity for the inhibitor activity is bound. Enzymes available for this use include, for example, the human serine proteases trypsin and chymotrypsin. Once the protease inhibitor is captured on the beads, the protein may be eluted using acid conditions, such as a low pH environment in the range of about 1.0 to about 5.0, preferably 1.25. The eluted protein may be substantially purified, i.e., recovered at least 70%, preferably 80%, more preferably 90%, most preferably at least 95%, as measured by high performance liquid chromatography (HPLC) (e.g., a C4 column using a 60% acetonitrile 0.1%/trifluoroacetic acid elution gradient.

D. Antibody Preparation

Antibodies specific against β-amyloid core protein and β-amyloid-related proteins are prepared by known procedures. As an example using synthetic peptides, typically the protein sequence is analysed for regions of at least about 10 amino acids long which have predominantly polar and/or charged amino acid residues to identify favorable immunogenic regions.

As another example, the DNA sequence shown in FIG. 1 can be used to design oligopeptides which are specific to the inserted sequence in λAPCP168i4, as well as the corresponding junction of this insert to the β-amyloid-related protein described by Kang et al. For example, an oligopeptide spanning the inserted junction such as Glu-Glu-Val-Val-Arg-Val-Pro-Thr-Thr-Ala may be used to immunize animals to produce a specific antisera against this region of the protein described by Kang et al. Inspection of the Kang et al. sequence in the absence of knowledge of the λAPCP168i4 sequence would not provide the information necessary to identify this peptide as a valuable reagent by any method known in the art. As another example, oligopeptides designed to represent sequences present in the 168 basepair insert region could be used in a similar manner to generate antisera against this unique region of the APCP168i4 protein. Thus, the regions identified as favorable for immunogenicity are synthesized by conventional peptide synthetic methods, and coupled covalently to a suitable carrier protein, such as keyhole limpet hemocyanin. Antibodies are raised against the peptide/protein conjugate in rabbits or the like by conventional methods. The presence of antibody in immunized animals is detected by standard methods, such as immunoreactivity to the immunizing synthetic peptide affixed to a microtiter plate, followed by ELISA.

Another method of antibody production uses the bacterially produced β-amyloid-related fusion protein of Example 2 as the immunogen. The immunogenicity of this protein is shown by the immunoreactivity of the antisera to the bacterially produced fusion protein.

Yet another method of antibody production relies on the inoculation of the host animal with a live recombinant vaccinia virus encoding β-amyloid-related protein, such recombinant viruses being generated by established techniques involving recombination between wild-type vaccinia virus and the vectors derived from pSCll, such as pFL4T4BV, described herein. These antibodies can then be used in the diagnostic assays described below.

A panel of antibodies which are specific against peptides derived from different regions of the β-amyloid-related protein, such as the A4i peptide, are further analysed for immunoreactivity of β-amyloid-related proteins present in the serum or cerebral spinal fluid of patients with Alzheimer's disease, to identify antibodies suitable for a diagnostic assay for Alzheimer's disease, as discussed below.

E. Diagnostic and Prognostic Methods

The DNA sequences described in FIGS. 3, 4, and 6 for β-amyloid-related protein are primarily derived from an apparently normal advanced-age male showing no signs of Alzheimer's disease at the time of death. The λAPCP168i4 sequence described in FIG. 1 for another β-amyloid-related protein is derived from cultured fibroblast cells. These sequences provide a standard for identifying mutations in genomic sequences which are found in individuals with Alzheimer's disease, and which are therefore likely to be associated with a predisposition to the disease.

1. Prognostic Methods. Assays are used to determine an individual's genetic predisposition to Alzheimer's disease. These tests use the DNA sequences of the present invention in a comparative study with samples of the patient's DNA to define polymorphism in the region of the chromosome containing the β-amyloid gene. Alternatively or concurrently, the DNA sequences of the present invention can be used in nucleic acid hybridization analysis to define alterations, which alterations are meant to include additions, deletions, mutations or substitutions, in the DNA or RNA encoding β-amyloid-related proteins.

Alterations in the β-amyloid-related protein sequences which correlate with Alzheimer's disease can be assayed by a differential probe binding method. Under appropriate hybridization conditions, known in the art, the oligonucleotide probes will bind to completely complementary sequences, but not to closely related but altered sequences.

In one assay method, nucleic acid samples prepared from the test subject are hybridized with each probe, under the defined hybridization conditions, and examined for binding to specific oligonucleotides. Alterations, and thus predisposition to Alzheimer disease, are confirmed by binding one probe, but not to the other probe. The probe-binding method, as it has been applied to other genetic diseases, is described in Conner, B.J., et al., *Proc Nat Acad Sci* (USA) (1983) 80:278-282.

Alternatively, probes derived from the genomic or cDNA sequences described above may be used to identify restriction fragment length polymorphisms which are associated with a genetic predisposition to Alzheimer's disease. Initially the probes are used to identify restriction site fragment lengths from both normal and diseased genomic digest samples. Changes in restriction fragment lengths which correlate with Alzheimer's disease are then applied to genetic screening, by standard methods. That is, test subject genomic material is digested with the restriction enzyme(s) of interest, and the fragment pattern on Southern blotting is determined with the labeled probe.

2. Diagnostic Methods. In various other clinical amyloidoses, the amyloidogenic peptides are variants of normally expressed gene products. These peptides have been altered either by aberrant proteolytic processing or by genetic lesions yielding an alteration in the primary amino acid sequences. There are known amyloidosis, such as Familial Amyloid Polyneuropathy (FAP), in which a mixture of the normal precursor and the amyloidogenic variant coexist within the circulation. An aberrant tissue-distribution for the expression of the aberrant gene product, or some other alteration in its level of expression, its sequence, or its processing in Alzheimer's disease could have significance in terms of the etiology of amyloid deposition.

A first diagnostic test which utilizes the materials of the invention is a direct antibody assay for the increase or decrease of β-amyloid core protein or β-amyloid-related proteins in Alzheimer's individuals relative to normal individuals. In this method, antibodies obtained as described above are screened for specific immunoreactivity with proteins from individuals known to have Alzheimer's disease. The presence of immunoreactive serum proteins is determined by standard immunoassay techniques, such as solid-phase ELISA techniques.

The body sample which is assayed for the presence of β-amyloid core protein or β-amyloid-related protein is, for example, serum or cerebral spinal fluid. For instance, in hereditary cerebral hemorrhage with amyloidosis, a disorder wherein the amyloid is generated from the gamma-trace precursor, the precursor can be detected in cerebrospinal fluid using an immunoassay. The levels of the precursor are reduced in the patients having the disease, leading to the conclusion that it is used up during the formation of the deposits. The precursor is made in the brain, and hence the cerebrospinal fluid is the appropriate sample.

In another diagnostic test, DNA encoding β-amyloid-related protein is directly useful as a probe to detect an increase or decrease in synthesis of mRNAs encoding β-amyloid-related proteins in the appropriate target cells by virtue of its ability to hybridize to the appropriate mRNA. An example showing the utility of this method is given in Example 5 below.

A third diagnostic assay permits the detection of antibodies against the amyloid protein in patient's serum using such standard ELISA techniques wherein the purified recombinant amyloid protein or synthetic peptide is bound to the solid support.

F. Therapeutic Methods

The invention also provides for improved therapeutic treatments for Alzheimer's disease One therapeutic treatment is suggested by the sequence of the A4i protein encoded by the 168 bp insert in λAPCP168i4.

By comparing the degree of relatedness of one protein to another, the amino acid sequence of the A4i protein was found to be homologous to a family of proteins known as Kunitz-type basic protease inhibitors. The level of relatedness of the insert protein segment to three members of the Kunitz family is shown in FIG. 13, where the symbol (:) indicates an identity between the two sequences compared and the symbol (.) indicates the substitution of an amino acid with similar chemical properties.

The comparison showed that the insert sequence depicted by the one-letter amino acid code as EVCS . . . GSAI is related to a high degree over its entire length to all members of the Kunitz family (only three are shown as an example). The three comparisons shown in FIGS. 13-1 and 13-2 are to: (1) a human trypsin inhibitor, a secreted plasma protein which inhibits trypsin, plasmin and lysosomal granulocytic elastase (Wachter, E., and Hochstrasser, K. *Hoppe-Seyler's Z Physiol Chem* (1981) 362:1351–1355; Morii, M., and Travis, *J. Biol Chem Hocce-Seyler* (1985) 366:19–21; (2) a bovine trypsin inhibitor which inhibits trypsin, chymotrypsin, elastases and plasmin (Hochstrasser, K. and Wachter, E., *Hoppe-Seyler's Z Physiol Chem* (1983) 364:1679–1687; Hochstrasser, K., et al., *Hoppe-Seyler's Z Physiol Chem* (1983) 364:1689–1696; and (3) a bovine serum basic protease inhibitor (and its precursor) which inhibits trypsin, kallikrein, chymotrypsin, and plasmin (Anderson, S. and Kingston, I.B. *Proc Nat Acad Sci (USA)* (1983) 80:6838–6842. Based on this level of relatedness to the A4i protein sequence, one interpretation is that this region of the λAPCP168i4 protein functions as a protease inhibitor in vivo.

Alzheimer's disease has been associated with the formation of amyloid plaques. Further, amyloid is formed as a result of the proteolysis of the β-amyloid precursor protein. The A4i protein is believed to prevent the cleavage of the β-amyloid precursor thus preventing the formation of the β-amyloid protein. Reducing the amount of β-amyloid formed may reduce plaque formation.

The present invention is not bound by the above interpretation. An alternative mechanism of action for the inhibitor which would give the same result (reduced plaque formation) via a different mechanism can be provided. The A4i protein could act as a protease inhibitor and inhibit a protease which degrades the plaque. Administration of an antagonist, for example a peptide or a specific antibody (either monoclonal or polyclonal) that is specific for the inhibitor to block the interaction of the inhibitor to the protease would allow for the plaque to be degraded and as such be therapeutically useful.

The A4i inhibitor or other inhibitors, peptidic or non-peptidic, could be used to treat or prevent Alzheimer's disease by a mechanism such as preventing the formation of neuritic plaques or allowing the plaque formed to be readily degraded. One method of administration might involve nasal delivery of such a peptide which would provide for transmucosal delivery and thus avoid the GI tract and the destruction of the peptide therein. Nasal delivery systems could be produced by formulating a solution containing the protease inhibitor peptide with one or more excipients and an effective amount of an adjuvant, such as the fusidic acid derivatives or a polyoxyethylene ether at a concentration in the range of about 0.1–10% (w/w). It should be pointed out that the effectiveness of A4i may be dependent on or be influenced by the ability to deliver the inhibitor locally to the brain. If delivery to the brain is needed, special considerations related to the blood-brain barrier must be dealt with because exchange of materials across the cerebral vessels is different from that in other capillary beds. Attaching the A4i to delivery vehicles known to enhance delivery of material across the blood-brain barrier might be useful. Stabilizers, preservatives and other components normally present in nasal delivery systems could optionally be added. The amount of peptide would vary, depending on its efficacy and bioavailability, but could range from about 0.1–25% (w/w).

The nasal systems could be administered by spraying from 10–100 μl of the solution into each side of the nose from 1–4 times a day. However, it should be noted that dosing could also be more or less frequent and would be adjusted during use depending upon the needs of the particular patient. Other modes of delivery include a solution of inhibitor in a pharmaceutically acceptable excipient where the inhibitor is 0.1–25% (w/w) and where the inhibitor is administered by injection into the cerebrospinal fluid, or directly onto the brain. A more localized administration to the central nervous system is believed to be preferred. However, if plaques accumulate systemically, the inhibitor may be administered intravenously. Further, if the inhibitor is non-peptidic, oral dosing may be possible.

The A4i protein and analogs thereof have applicability outside the treatment of Alzheimer's disease as indicated by their specificity profile. For example, it has been found that the A4i of the present invention strongly inhibits plasmin and tryptase, and also inhibits pancreatic trypsin, α-chymotrypsin, tissue kallikrein and serum kallikrein. The inhibitor did not inhibit chymase, pancreatic elastase, α-thrombin, urokinase, papain or cathepsin B. In acute pancreatitis, there is a general release of digestive proteases such as trypsin, chymotrypsin and elastase, from the pancreas into the circulation. It would be useful in the clinical management of pancreatitis to administer A4i with one or more protease inhibitors systemically to inactivate these proteases.

It is pointed out that aprotinin, a bovine-derived protease inhibitor sharing approximately 50% amino acid homology with the present A4i inhibitor, has been found to have clinical utility in animal models (H. Fritz and G. Wunderer, *Drug Res* 33(I), No. 4 (1983) pp. 479-494). The bovine inhibitor, sold under the Trademark Trasylol, is marketed in Europe for use in connection with acute pancreatis One advantage of the A4i over a bovine inhibitor is that A4i is naturally present in low levels in the circulation in the form of its larger precursor Accordingly, A4i would not generate an allergic or immune reaction as might be expected with aprotinin or other inhibitors of non-human origin.

The significant affinity of A4i for the plasma proteases plasmin and tryptase makes possible the in vivo regulation of specific coagulation factors. Plasmin is important in lysing fibrin clots (i.e. fibrinolysis) whereas tryptase is involved in clot formation. Administration of effective dosages of the A4i would aid in regulating clot formation and clot dissolution.

Fibrin glue used in wound healing contains aprotinin which could be replaced with A4i. Accordingly, A4i polypeptide may be employed to augment tissue repair necessary for wound healing. The strong affinity of A4i for plasmin is believed to interfere with plasmin's fibrinolytic activity. This activity is particularly effective when A4i is used in an adhesion fibrin ("fibrin glue") for adapting tissues and sealing bleeding areas with fibrin, preventing its dissolution before tissue repair has set in such as with surgical lacerations.

The strong affinity of the A4i polypeptide for tryptase makes the inhibitor directly useful in anticoagulant treatments by inhibiting prothrombin activation in vivo. The dissociation constant of A4i is $K_i = 2.2 \times 10^{-10}$ which is similar to that reported for mast cell trypstatin on tryptase (Kido et al., *J Biol Chem* 263:18104-18107 (1988)), which has been shown to effectively inhibit the amidase activities of mast cell tryptase. Thus, A4i can be employed as an exogenously administered thrombolytic agent.

Generally, an inhibitor composition is applied to the site of the wound by soaking a nonadhesive surgical dressing in the composition or alternatively, by incorporating the composition into a slow-release matrix and applying it at the site of the wound.

A pharmaceutical composition may be made from the purified inhibitor in a conventional way, with or without the use of additives such as sodium chloride, glucose, mannitol, albumin, and the like. The compositions will mostly be suitable for parenteral administration, including intravenous or intraarterial injection or infusion.

The resulting composition may be administered to patients in a suitable dose and may be used prophylactically to prevent acute and chronic thromboembolic occlusions of different vascular beds, such as encountered in deep vein thrombosis, pulmonary embolism, myocardial infarction, stroke, arterial occlusion, extracorporeal circulation and arteriovenous shunts. For this purpose it would be necessary to insure that the A4i acts specifically on tryptase and would not be a significant inhibitor of plasmin.

The involvement of plasmin in the liberation of cancer cells from cancerous tissue has been observed. Inhibition of plasmin and other proteases with A4i may significantly reduce or prevent tumor growth.

Proteases found in normal tissues may be produced in excess and be involved in tissue inflammation and damage. Inhibition of protease release might lead to reduced tissue damage and inflammation. Allergic reactions causing release of protease would also be amenable to treatment by protease inhibition.

Other forms of the present A4i protein are provided herein. These other forms are analogs of A4i, which is the 57 amino acid protease inhibitor. These analogs contain at least one amino acid substitution which is effective to yield an inhibitor having altered protease specificity. The residue termed $P_1$ is known to play a major role in defining the specificity of a protease inhibitor. In the mature secreted inhibitor of the invention, this $P_1$ residue is $Arg_{13}$ which is expected to direct this inhibitor to enzymes having trypsin-like activities.

By analogy to aprotinin, wherein it has been shown that modification to its $P_1$ residue has modified the protease activity of the inhibitor (see Gebhard, W., et al., in *Proteinase Inhibitors*, eds. Barrett and Salvesin, Amsterdam, N.Y., Oxford: Elsevier 1986), modification via site-specific mutagenesis of the present inhibitor produces similar results. For enhanced inhibition of enzymes having chymotrypsin activity, $Arg_{13}$ of the present inhibitor is substituted with aromatic amino acids such as, for example, Phe, Tyr and Trp; whereas to produce an inhibitor having enhanced ability to inhibit enzymes possessing human elastase activity, the $Arg_{13}$ residue is substituted with neutral hydrophobic amino acids such as, for example, Leu, Met and Val.

The analogs of the present protease inhibitors are constructed from oligonucleotides containing the specific codons encoding the desired amino acid at this location, using site-specific mutagenesis techniques as are known in the art. The desired activities of the analogs thus constructed are assayed using the appropriate enzyme, for example, either trypsin, chymotrypsin or elastase as the standard in one of the respective assays using, for example, the trypsin or chymotrypsin assays described in Tan, N.H. *Biochem* (1977) 16:1531-1541 and the elastase assays in Barrett, A.J. (1981) in *Methods in Enzymology* vol. 80, L. Lorand ed., Academic Press, New York. The activity of the analogs may be compared with that of the natural protease inhibitor of the invention. The kinetics of inhibition ($K_i$) of the natural protease inhibitor for trypsin ($K^i = 3 \times 10^{-9}M$) and chymotrypsin ($8.5 \times 10^{-9}M$) are in the nanomolar range and therefore, quite specific.

G. Methods and Materials

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both procaryotic and eucaryotic systems may be used to express the β-amyloid core and β-amyloid-related sequences; procaryotic hosts are, of course, the most convenient for cloning procedures. Procaryotes most frequently are represented by various strains of *E. coli*: however, other microbial strains may also be used. *E. coli* strains may secrete the β-amyloid core and β-amyloid-related proteins to the periplasm when the genes encoding these proteins are fused to appropriate signal peptides, and certain *E. coli* strains, for example, a lipoprotein mutant strain such as JE5505 (Kanamari, T. *Gene* (1988) 66:295-300), will excrete the chimeric proteins directly to the culture medium.

Plasmid vectors which contain replication sites, selectable markers and control sequences derived from a species compatible with the host are used; for example, *E. coli* is typically transformed using derivatives of pBR322, a plasmid derived from an *E. coli* species by Bolivar et al., *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the β-lactamase (penicillinase) and lactose (lac) promoter systems (Chang et al., *Nature* (1977) 198:1056) and the tryptophan (trp) promoter system (Goeddel et al. *Nucleic Acids Res* (1980) 8:4057) and the lambda-derived $P_L$ promoter and N-gene ribosome binding site (Shimatake et al., *Nature* (1981) 292:128).

Other procaryotic control sequences include signal sequences which direct secretion of a protein to the periplasm. Commonly used bacterial signal peptides include the ompA (Kikuchi et al., *Nucleic Acids Res* (1981) 9:5671-5678) and phoA (Beck and Bremer, *Nucleic Acids Res* (1980) 8:3011-3024) signal peptides which can be fused to the protease inhibitor sequence of the invention.

In addition to bacteria, eucaryotic microbes, such as yeast, may also be used as hosts. Laboratory strains of *Saccharomyces cerevisiae*. Baker's yeast, are most used although a number of other strains or species are commonly available. Vectors employing, for example, the 2 μ origin of replication of Broach, J. R., *Meth Enz* (1983) 101:307, or other yeast compatible origins of replication (see, for example, Stinchcomb et al., *Nature* (1979) 282:39, Tschumper, G., et al., *Gene* (1980) 10:157 and Clarke, L., et al., *Meth Enz* (1983) 101:300) may be used. Control sequences for yeast vectors include promoters for the synthesis of glycolytic enzymes (Hess et al., *J Adv Enzyme Req* (1968) 7:149; Holland et al., *Biochemistry* (1978) 17:4900). Additional promoters known in the art include the promoter for 3-phosphoglycerate kinase (Hitzeman et al., *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel et al., U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., *Nature* (1978) 273:113), or other viral promoters such as those derived from polyoma, Adenovirus 2, bovine papilloma virus, or avian sarcoma viruses. The controllable promoter, hMTII (Karin, M., et al., *Nature* (1982) 299:797-802) may also be used. General aspects of mammalian cell host system transformations have been described by Axel (supra). It now appears, also that "enhancer" regions are important in optimizing expression; these are, generally, sequences found upstream or downstream of the promoter region in noncoding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S.N., *Proc Natl Acad Sci (USA)* (1972) 69:2110, or the $RbCl_2$ method described in Maniatis et al., *Molecular Cloning: A Laboratory Manual* (1982) Cold Spring Harbor Press, p. 254 and Hanahan, D., *J Mol Biol* (1983) 166:557-580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al., *Cell* (1979) 16:777-785 may be used. Transformations into yeast may be carried out according to the method of Beggs, J.D., *Nature* (1978) 275:104-109 or of Hinnen, A., et al., *Proc Natl Acad Sci (USA)* (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; Jay, Ernest, *J Biol Chem* (1984) 259:6311.

Synthetic oligonucleotides are prepared by either the phosphotriester method as described by Edge, et al., *Nature* (supra) and Duckworth et al., *Nucleic Acids Res* (1981) 9:1691 or the phosphoramidite method as described by Beaucage, S.L., and Caruthers, M.H., *Tet Letts* (1981) 22:1859 and Matteucci, M.D., and Caruthers, M.H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles $\gamma$32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTps within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15-50 $\mu$l volumes under the following standard conditions and temperatures: for example, 20 mM Tris-HCl pH 7.5, 10 mM $MgCl_2$, 10 mM DTT, 33 $\mu$g/ml BSA, 10 mM-50 mM NaCl, and either 40 $\mu$M ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 $\mu$g/ml total DNA concentrations (5-100 nM total end concentration). Intermolecular blunt end ligations are performed at 1 $\mu$M total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per $\mu$g of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M.J., and Smith, M. *Nucleic Acids Res* (1982) 10:6487-6500 and Adelman, J.P., et al., *DNA* (1983) 2:183-193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

In the constructions set forth below, correct ligations for plasmid construction are confirmed by first transforming *E. coli* strain MC1061 obtained from Dr. M. Casadaban (Casadaban, M., et al., *J Mol Biol* (1980) 138:179-207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D.B., et al., *Proc Natl Acad Sci (USA)* (1969) 62:1159, optionally following chloramphenicol amplification (Clewell, D.B., *J Bacteriol* (1972) 110:667). Several mini DNA preps are commonly used, e.g., Holmes, D.S., et al., *Anal Biochem* (1981)

114:193–197 and Birnboim, H.C., et al., *Nucleic Acids Res* (1979) 7:1513–1523. The isolated DNA is analyzed by restriction and/or sequenced by the dideoxy nucleotide method of Sanger, F., et al., *Proc Natl Acad Sci (USA)* (1977) 74:5463 as further described by Messing et al., *Nucleic Acids Res* (1981) 9:309, or by the method of Maxam et al., *Methods in Enzymology* (1980) 65:499.

The invention will be further described by the following examples. These are provided only to illustrate embodiments of the invention and are not to be construed as limitations on the invention's scope.

EXAMPLE 1

Isolation of a Genomic Clone and cDNA Clones Encoding β-amyloid Core Protein and β-amyloid-related Proteins A human genomic library in Charon 4A λ-phage was screened using a six-fold degenerate 38 mer probe corresponding to the first 13 amino acids of the 28 amino acid sequence N-terminal sequence. This probe,

```
3' CTGCGACTTAAGGCCGTGCTGAGICCGATGCTTCAGGTT-5'
                    G
                    T
``` wherein I is inosine, when used to screen the human genomic library yielded a strongly hybridizing colony designated λSM2. λSM2 DNA was isolated and partially sequenced with the results shown in FIG. 2. The sequenced portion is only a small fraction of the approximately 10–20 kb insert in the phage isolated from the genomic library.

A probe was constructed from the HindIII/RsaI fragment representing approximately positions 201–294. The genomic probe was used to screen a cDNA library prepared in λgt10 using standard techniques from brain tissue of a 55 year old man with no evidence of Alzheimer's disease. The three clones designated λSM2W4, λSM2W3 and λSM2W9 were identified.

EXAMPLE 2

The genomic and cDNA sequences described above can be used to prepare recombinant protein in an efficient expression system. Genomic DNA can be utilized in cells, such as mammalian cells, capable of processing introns. Bacterial cells can be utilized for expression of cDNA sequences.

Bacterial Expression of β-Amyloid-Related Protein and Production of Antisera

A. Construction of plasmid pAPCP118-3

Construction of an *E. coli* expression vector for human β-amyloid-related protein (655–751) required the joining of three DNA fragments: (1) a plasmid backbone (consisting of replication functions, ampicillin resistance gene, tryptophan promoter/operator, ribosome binding site, DNA encoding the amino terminus of *E. coli* β-galactosidase (7 amino acids) followed by six threonine residues, and transcription termination signals), (2) a fragment of the β-amyloid-related DNA encoding amino acids 655–728, of FIG. 1 and (3) a synthetic fragment of the β-amyloid-related DNA encoding amino acids 729–751 of FIG. 1 and the stop codon UAA.

The plasmid backbone referred to above is derived from pTRP83-1. Plasmid pTRP83-1 is a bacterial expression plasmid which was constructed in the following manner:

1. Construction of the Synthetic Tryptophan Operon Promoter and Operator Regulatory Sequence The ten oligodeoxynucleotides shown in FIG. 14 were synthesized by the phosphotriester method and purified. 500 pmole of each oligodeoxynucleotide except 1 and 10 were phosphorylated individually in 20 μl containing 60 mM Tris-HCl, pH 8, 15 mM DTT, 10 mM MgCl$_2$, 20 μCi of [λ-$^{32}$p]-ATP and 20 units of polynucleotide kinase (P/L Biochemicals) for 30 min. at 37° C. This was followed by the addition of 10 μl containing 60 mM Tris-HCl, pH 8, 15 mM DTT, 10 mM MgCl$_2$, 1.5 mM ATP and 20 additional units of polynucleotide kinase followed by another 30 min incubation at 37° C. Following incubation the samples were incubated at 100° C. for 5 min. 500 pmole of oligodeoxynucleotides 1 and 10 were diluted to 30 μl in the above buffer without ATP.

16.7 pmole of each oligodeoxynucleotide constituting a double stranded pair (e.g. oligodeoxynucleotides 1 and 2, 3 and 4 etc. FIG. 14 were mixed and incubated at 90° C. for 2 min followed by slow cooling to room temperature. Each pair was then combined with the others in the construction and extracted with phenol/chloroform followed by ethanol precipitation. The oligodeoxynucleotide pairs were reconstituted in 30 μl containing 5 mM Tris-HCl, pH 8, 10 mM MgCl$_2$, 20 mM DTT, heated to 50° C. for 10 min and allowed to cool to room temperature followed by the addition of ATP to a final concentration of 0.5 mM. 800 units of T4 DNA ligase were then added and the mixture incubated at 12.5° C. for 12–16 hours.

The ligation mixture was extracted with phenol/chloroform and the DNA ethanol precipitated. The dried DNA was reconstituted in 30 μl and digested with EcoRI and PstI for 1 hour at 37° C. The mixture was extracted with phenol/chloroform and ethanol precipitated followed by separation of the various double stranded DNA segments by electrophoresis on an 8% polyacrylamide gel, according to the method of Laemmli et al., *Nature* (1970) 227:680. The DNA fragments were visualized by wet gel autoradiography and a band corresponding to approximately 100 bp in length was cut out and eluted overnight as described. The excised synthetic DNA fragment was ligated to plasmids M13-mp8 or M13-mp9 (Messing and Vieira, (1982) *Gene* 19:259–268) similarly digested with EcoRI and PstI, and submitted to dideoxynucleotide sequence analysis to confirm the designed sequence. This designed sequence contains the promoter (−35 and −10 regions) and operator regions of the tryptophan operon (trp) as well as the ribosome binding region of the tryptophan operon leader peptide. Analogous sequences to that shown in FIG. 14 have been proven to be useful in the expression of heterologous proteins in *E. coli* (Hallewell, R.A., and Emtage, S., *Gene* (1980) 9:27–47, Ikehara, M., et al., *Proc Natl Acad Sci (USA)* (1984) 81:5956–5960).

2. Construction of the Synthetic trp Promoter/Operator Containing Plasmid pTRP233

Plasmid pKK233-2 (Amann, E. and Brosius, J., *Gene* (1985) 40:183 was digested to completion with NdeI and the ends were made blunt with 5 units of *E. coli* polymerase I, Klenow fragment (Boehringer-Mannheim, Inc.) and the addition of all four dNTPs to 50 μM. This was incubated at 25° C. for 20 min. Following phenol/chloroform extraction and ethanol precipitation, the NdeI-digested DNA was ligated and transformed into *E. coli* (Nakamura, K., et al., *J Mol Acpl Genet* (1982) 1:289-299). The resulting plasmid lacking the NdeI site was designated pKK-233-2-Nde.

Twenty nanograms of plasmid pKK-233-2-Nde was digested to completion with EcoRI and PstI followed by calf intestinal phosphatase treatment. Fifty nanograms of the synthetic trp promoter/operator sequence obtained from M13 RF, by digesting with EcoRI and PstI, were mixed with ten nanograms of EcoRI and PstI-digested pKK-233-2-Nde and ligated with T4-DNA ligase, followed by transformation into *E. coli* JA221 lpp−/I'lacI. Transformants were screened for the presence of plasmid DNA containing the 100 bp EcoRI-PstI synthetic trp promoter/operator; the correct plasmid was then isolated and designated pTRP233.

pTrRP233 was digested with EcoRI, the ends blunted with Klenow, and ligated to remove the EcoRI restriction site. The plasmid was next digested with NdeI and HindIII and an NdeI-EcoRI-HindIII fragment encoding β-gal-(thr)6 between the NdeI and EcoRI sites was inserted to create plasmid pTRP83-1.

Plasmid pTRP83-1 was then digested with EcoRI and HindIII restriction endonucleases and the digest was electrophoresed in a 0.6% agarose gel (Maniatis, T., et al , at pp. 157-160). The large fragment containing the plasmid backbone was eluted from the gel. Next, the EcoRI fragment containing β-amyloid-related sequences derived from λSM2W3 (corresponding to amino acids 655-751 of FIG. 1 and 500 bp of 3′-untranslated sequences) was digested next with HaeII restriction endonuclease and electrophoresed in a 12% polyacrylamide gel. The approximately 230 bp EcoRI-HaeII fragment (containing β-amyloid-related sequences encoding amino acids 655-728) was eluted. The remaining portion of the β-amyloid-related sequences of FIG. 1 encoding amino acids from 728-751 were prepared using the six oligodeoxynucleotides illustrated in FIG. 9. 500 pmole of each oligodeoxynucleotide except for 1 and 6 were phosphorylated individually. 167 pmole of each oligodeoxynucleotide constituting a pair (e.g. 1 and 2, 2 and 3, etc.) were mixed and incubated at 90° C. for 2 min followed by slow cooling to room temperature. Each pair was then combined with the others and extracted with phenol/chloroform followed by ethanol precipitation. The pairs were reconstituted in 30 μl containing 5 mM Tris-HCl, pH 8, 10 mM $MgCl_2$, 20 mM DTT, heated to 50° C. for 10 min, and allowed to cool to room temperature. ATP was added to a final concentration of 0.5 mM, 800 units of T4 DNA ligase was added and the mixture incubated at 12° C. for 12-16 hr. The ligation was electrophoresed in a 12% polyacrylamide gel and the 79 bp HaeII-HindIII synthetic fragment was eluted.

The EcoRI-HindIII plasmid backbone of pTRP83-1, the approximately 230 bp EcoRI-HaeII β-amyloid cDNA fragment, and the 79 bp synthetic HaeII-HindIII β-amyloid fragment were ligated at 12° C. for 12-16 hr. *E. coli* strain MC1061 was transformed with the ligation mixture (Maniatis, T., et al., pp. 250-251) and the resulting ampicillin resistant colonies were grown overnight in 1 ml of L broth supplemented with 100 μg/ml ampicillin sulfate. Plasmid DNA was prepared by the alkaline lysis method (Maniatis et al., pp. 368-369). Plasmids were screened for the correct inserts by digestion with EcoRI and HindIII. A plasmid releasing an approximately 300 bp EcoRI-HindIII fragment was designated pAPCP118-3.

B. Expression of β-Amyloid-Related Fusion Polypeptide (655-751)

The plasmid pAPCP118-3 expresses a 110 amino acid β-galactosidase-threonine-β-amyloid-related fusion protein under the control of the *E. coli* tryptophan promoter/operator. *E. coli* strain W3110 was transformed with plasmid pAPCP118-3 and one of the resulting ampicillin resistant colonies was grown for 12-16 hr at 37° C. in media containing M9 minimal salts (Miller, J., Experiments in Molecular Genetics, Cold Spring Harbor Laboratory, Cold Spring Harbor, N.Y.) supplemented with glucose (0.4%), thiamine (2 μg/ml), $MgSO_4 \cdot 7H_2O$ (200 μg/ml), tryptophan (40 μg/ml), casamino acids (0.5%), and ampicillin (100 μg/ml). Expression was induced by dilution of the culture 100-fold into new media with reduced tryptophan (4 μg/ml) for 2 hr followed by the addition of 3-8-indoleacrylic acid at a final concentration of 25 μg/ml. Expression of β-gal-thr-β-amyloid (655-751) fusion protein occurs at the level of 10-20% of total cell protein, and is present in the form of inclusion bodies which can be visualized by phase contrast microscopy (1000×magnification). The cells were harvested 6 hr after the addition of the 3-β-indoleacrylic acid by centrifugation, washed with 10 mM Tris-HCl, pH 7.5, and the cell pellet frozen at −20° C.

C. Purification of Beta-gal-thr-β-Amyloid (655-751) Fusion Protein for Preparation of Antiserum A cell pellet from 500 ml of culture was resuspended in 40 ml of 10 mM Tris-HCl, pH 7.5, 0.6 M NaCl, and incubated with 8 mg of lysozyme and the protease inhibitors phenylmethylsulfonylfluoride (PMSF) and aprotinin (0.5 mM and 25 μg/ml respectively) for 10 min at 4° C. Solutions of the two detergents, sodium deoxycholate (480 μl of 10% solution) and NP-40 (240 μl of 20% solution), were then added for an additional 10 min incubation at 4° C. The cell pellet was sonicated to disrupt cells and free inclusion bodies. RNAse (10 μg/ml) DNAse (10 μg/ml) were added and the mixture stirred for 30 min at room temperature to digest RNA and DNA. The inclusion bodies (and some cell debris) were collected by centrifugation for 10 min at 5000 rpm (SA600 rotor). The supernatant was discarded and the pellet boiled in protein gel sample buffer for 20 min to solubilize the fusion protein. The fusion protein was then purified by electrophoresis in 12% SDS/ polyacrylamide gels (Laemmli, U.K., *Nature* (1970) 227:680). The edges of each gel were removed and stained with Coomassie blue to visualize the 15 kilodalton (kD) fusion protein. They were then realigned with the gel so that the region of the gel containing the fusion protein could be excised. The polyacrylamide was then crushed through a series of needles (16 gauge down to 22 gauge) with the addition of physiological saline to keep the polyacrylamide moist. The polyacrylamide/- fusion protein crush was mixed with adjuvant [RIBI(-RAS)] just prior to immunization of the rabbits. Approximately 150-200 μg of fusion protein was administered per animal for the first immunization. Subsequent immunizations use 50-100 μg of fusion protein.

D. Western Blot Analysis of β-Amyloid Synpep Antisera Using Beta-gal-thr-β-Amyloid (655-751) Fusion Protein Cell pellets of *E. coli* W3110 (pAPCP118-3) and W3110 (pTRp83-1) cultures induced with 3-β-indoleacrylic acid were boiled in Laemmli gel sample buffer and electrophoresed in 12% SDS polyacrylamide. The second transformed strain is a negative control which contains all proteins except for the β-gal-thr-β-amyloid (655-741) fusion. The gels were then electroblotted to nitrocellulose, incubated first with APCP synpep antisera collected from immunized rabbits, and then incubated with $^{125}$I-Staphylococcus protein A to identify bound antibody (Johnson, D.A., et al., *Gene Anal Tech* (1984) 1:3). An autoradiogram was generated from these nitrocellulose filters which demonstrated crossreactivity between anti-APCP3 serum and the fusion protein, Synpep APCP3 is comprised of amino acids 705-719 of FIG. 1 which are included within the β-amyloid portion of the fusion protein. Cross-reactivity was also observed for other β-amyloid synpep antisera.

EXAMPLE 3

Generation of Polyclonal and Monoclonal Antibodies Against β-Amyloid-Related Protein Using Live Recombinant Vaccinia Virus

1. Construction of Plasmid cFL4T4B.

The construction of the plasmid which allowed for the generation of polyclonal and monoclonal antibodies is schematically represented in FIG. 10. Plasmid pGEM-3 TM (Promega-Biotec) was EcoRI-digested and treated with calf intestinal phosphatase in accordance with Maniatis et al. Fifty nanograms of the purified 1.06 kb EcoRI fragment derived from λAPCP168i4 were mixed with 10 nanograms EcoRI digested pGEM-3 TM and incubated with T4 DNA ligase in a total volume of 20 ul for 30 min at 25° C. *E. coli* strain MC1061 was made competent for transformation by the CaCl₂ method and transformed with the ligation mix. Resulting ampicillin resistant colonies were grown overnight in 2 ml L-amp broth from which plasmid DNA was prepared by the Triton lysis method (Maniatis et al.). Plasmids were screened for the correct orientation by digestion with HindIII. A plasmid having 150 and 3700 bp HindIII restriction fragments was chosen and designated p4BI. The resulting plasmid p4BI was digested with HindIII, religated with T4 ligase for 30 minutes at 25° C. and competent MC1061 cells were transformed with the ligation mixture. Plasmids were screened for loss of the 130 bp HindIII fragment by EcoRI digestion. A plasmid containing a single EcoRI site was chosen and designated p4BΔRI. Ten nanograms of plasmid p4BΔRI was EcoRI-digested, treated with calf intestinal alkaline phosphatase, and ligated with 100 nanograms of the purified ~2 kb EcoRI fragment derived from λAPCP168i4. The ligation mixture was used to transform competent MC1061 cells. Resulting ampicillin-resistant colonies were grown overnight in L-amp broth and plasmid DNA was prepared. Plasmids were screened for the correct orientation by digestion with BamHI and HindIII. A plasmid having a 1.5 kb BamHI and an ~1.5 kb BamHI-HindIII fragment was chosen and designated p4T4B. Plasmid p4T4B was digested with SmaI and XmnI and the resulting ~2.7 kb fragment was eluted from 0.8% agarose followed by ethanol precipitation, dryed in vacuo and resuspended in dH₂O.

Five μg of the vaccinia virus expression vector pSCll (Chakrabarti et al., *Mol Cell Biol* (1985) 5:3403-3409) were digested to completion with SmaI followed by treatment with calf intestinal phosphatase. Five hundred nanograms of the purified ~2.7 kb SmaI-XmnI fragment derived from p4T4B were mixed with fifty nanograms of SmaI-digested pSCll and incubated with T4 DNA ligase in a total volume of 20 μl for 16 hours at 15° C. overnight. *E. coli* strain MC1061 was transformed with the ligation mix. Resulting ampicillin resistant colonies were grown overnight and plasmid DNA was isolated by the rapid boiling method (Maniatis et al.). Plasmids were screened for insertion and correct orientation by digestion with EcoRI. A plasmid having both an ~2500 bp and an ~600 bp EcoRI fragment was chosen and designated pFL4T4BV.

Monoclonal and polyclonal antibodies against full length β-amyloid-related protein are generated by using a novel method described by Yilma, T., et al., (*Hybridoma* (1987) 6:329-337). Briefly, the method enables the production of antibodies to a specified protein without the need for a purified antigen (protein) in either the immunization or screening phase of the procedure. The methods make use of the vaccinia virus cloning vectors (Smith et al., *Nature* (1983) 302:490-495) which can be genetically engineered to carry isolated genes. The infectious recombinant vaccinia virus may then be used to immunize mice. Two weeks after infection, mice are sacrificed and their spleen cells are fused with myeloma cells for monoclonal antibody production as described in the classical approach developed by Kohler and Milstein *Nature* (1973) 256:495. Alternatively, rabbits can be conventionally immunized with the infectious vaccinia virus recombinant to generate polyclonal antisera.

Ten μg of plasmid p4T4BV is used to transfect CV-1 monkey kidney cells infected with wild-type vaccinia virus according to standard methods (Mackett et al., *J Virol* (1984) 49:857-864). TK⁻ recombinants are isolated by plaque assay on TK⁻ cells in the presence of 25 μg/ml Bromodeoxyuridine (BUdR). For plaque assays involving blue color production, as in the case of the pSCll vaccinia virus co-expression vector, 300 μg of X-Gal per milliliter is placed in the agarose overlay, and plaques visualized after 4-6 hrs at 37° C. Plaques are purified two to three times in succession. DNA from the recombinant virus is examined by restriction endonuclease analysis and DNA hybridization to $^{32}$P-nick-translated 2091 bp EcoRI fragment from λAPCP168i4 to confirm the predicted structure.

Recombinant virus carrying the complete β-amyloid-related cDNA sequence of λAPCP168i4 is isolated and amplified to high titer (1 × 10⁸⁻⁹ pfu/ml). These recombinant viruses are used to immunize rabbits and mice for the subsequent production of polyclonal and monoclonal antibodies respectively, against full length β-amyloid-related protein(s) using well established methods or they can be used for the direct expression of the recombinant protein. The various antisera are screened either for their ability to specifically immunoprecipitate the correct size protein from $^{35}$S-methionine-labeled CV-1 cells which have been infected with an β-amyloid-related protein virus recombinant or for their ability to detect denatured protein on a western blot of similar cells which have not been exposed to radiolabeled amino acid.

EXAMPLE 4

Expression of β-Amyloid-Related Protein (1–751) in Cultured Mammalian Cells

To facilitate the expression of β-amyloid-related protein in mammalian cells, a plasmid is constructed such that the coding segment for the protein is fused to a powerful regulated promoter derived from the human metallothionine II (hMTII) gene. This procedure is performed in two steps. First an expression vector pMTSV40 polyA Bam was derived from phGH-SV(10) vector by digestion of phGH-SV(10) with BamHI and SmaI restriction enzymes, followed by incubation with DNA polymerase I (Klenow fragment) in order to create blunt-ended molecules. The blunt ends are subsequently ligated to BamHI linkers, cut with BamHI, and religated to allow for recircularization. This step removes all of the human growth hormone genomic sequence from phGH-SV(10) except for most of the 3' untranslated region of the mRNA and genomic sequences encoding putative 3' transcriptional stop and processing signals. For the mammalian cell expression construct, pMTSV40 polyA Bam is BamHI-digested, then incubated with all four nucleotide triphosphates and with DNA polymerase I to create blunt ends. This fragment is subsequently ligated with the purified 2678 bp SmaI-XmnI fragment derived from p4T4B (described previously). The recombinant molecules are introduced into MC1061 by transformation.

Chinese hamster ovary (CHO)-K1 cells are grown in a medium composed of a 1:1 mixture of F12 medium and DME medium with 10% fetal calf serum. The competent cells are co-transformed with the recombinant expression vector and pSU2:NEO (Southern, P., et al., *J Mol Appl Genet* (1982) 1:327–341). pSV2:NEO contains a functional gene conferring resistance to the neomycin analog G418. In the transformation, 500 ng of pSV2:NEO and 5 μg of the recombinant vector are applied to a 60 mm dish of CHO cells as a calcium phosphate-DNA co-precipitate as described by Graham, F.L. and Van der Eb, A.J. *Virology* (1973) 52:456–467. Growth of the cells in the antibiotic G418 as described by Southern et al. will yield a pool of stably transfected CHO cells containing expression vector DNA with the capacity to express β-amyloid-related mRNA and protein.

EXAMPLE 5

Expression of β-Amyloid-Related protein (652–751) in Cultured Mammalian Cells

Figure 12:
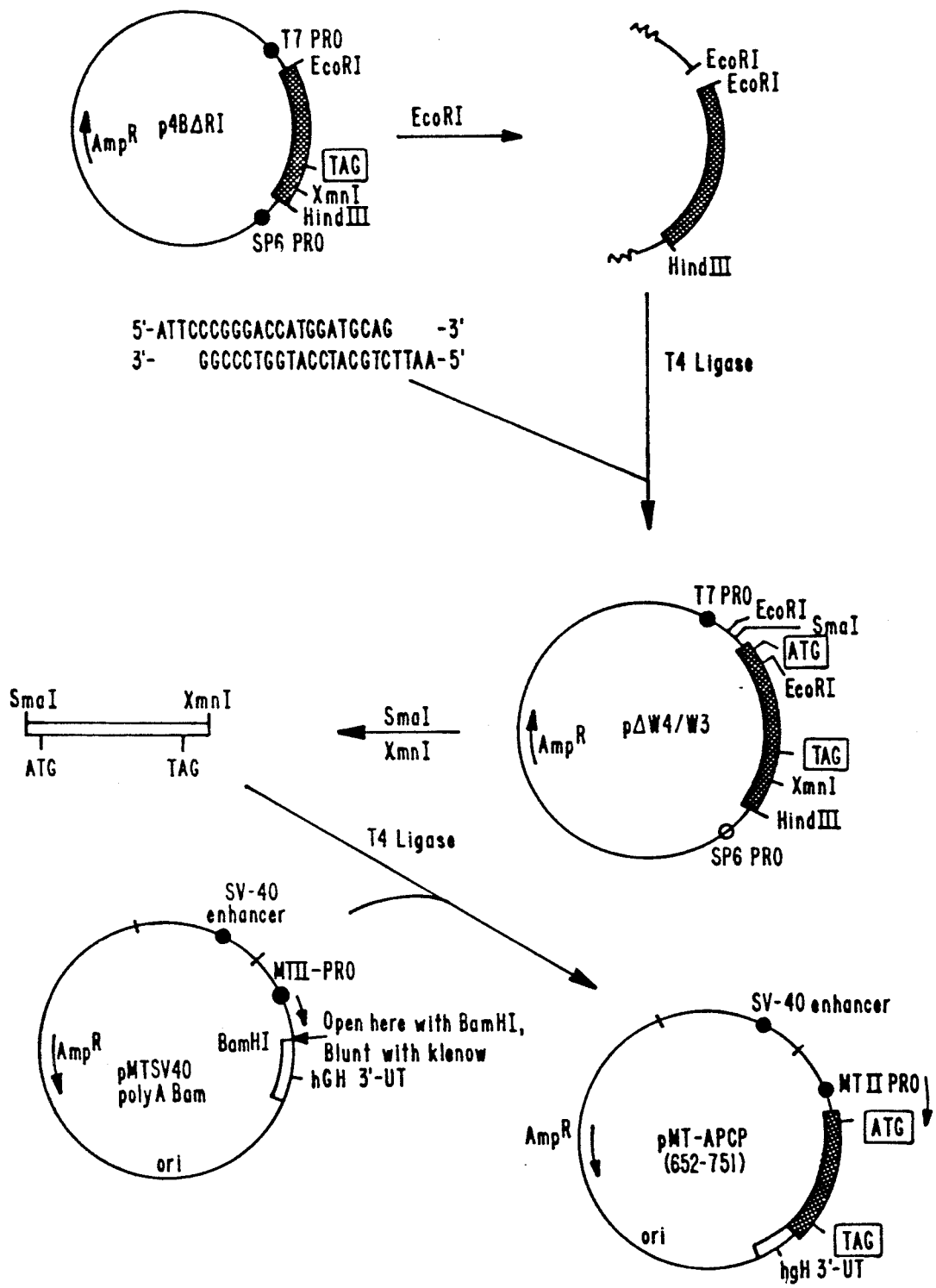
FIG. 12 shows the construction of an expression vector for the production of the β-amyloid-related protein described in FIG. 5, when the methionine encoded immediately upstream from the β-amyloid core protein sequence is used as an initiating methionine.

A mammalian cell expression vector encoding for the production of a β-amyloid-related protein can be constructed as shown in FIG. 12 as follows: the p4BΔRI vector of FIG. 10 is linearized by digestion with EcoRI. The vector is mixed with two oligonucleotides having the sequences:

```
5'-ATTCCCGGGACCATGGATGCAG-3'
3'-GGCCCTGGTACCTACGTCTTAA-5'
``` and ligated using T4 DNA ligase. These oligonucleotides reconstruct the Met-Asp-Ala codons of λSM2W4 and precede them by EcoRI and SmaI sites and follow them with another EcoRI site.

Competent *E. coli* strain DH1 cells are transformed with the mixture and ampicillin-resistant bacteria are selected by growth on L-Amp plates. A transformant containing the oligonucleotide pair inserted into the EcoRI site in the proper orientation is selected by standard screening techniques and designated pΔW4/W3. Plasmid DNA pΔW4/W3 is digested with SmaI and XmnI to remove sequences encoding the β-amyloid-related protein described in FIG. 5 and the correct piece is isolated by gel purification.

This piece can then be inserted into the mammalian cell expression vector pMTSV40 polyA Bam which has been linearized with BamHI and rendered blunt-ended as described above in Example 4. The resulting vector, pMT-APCP (652–751) can be used for the production of the β-amyloid-related protein (652–751).

EXAMPLE 6

Expression of β-Amyloid Precursor in Mammalian Cells

Outlined in Examples 4 and 5 are the construction of an expression system for the β-amyloid-related protein (1–751) driven by the human β-actin promoter. A nearly identical construct was prepared using the purified 2548 bp SmaI-XmnI fragment derived from p4T4B (described previously in Example 3) from which 116 bp from the 5' untranslated region have been deleted. This fragment was inserted into the SalI site behind the human β-actin promoter on a plasmid harboring the neomycin selectable marker for mammalian cell expression and the ampicillin resistance gene for selection of bacterial transformants. This vector, pHbAPr-1-neo, has been described by Gunning et al. (*Proc Nat'l Acad Sci USA* (1987) 84:4831–4835) and has been modified to remove the EcoRI site from the body of the original vector and to substitute the original polylinker region with a new polylinker containing an EcoRI site in addition to the SalI, HindIII, and BamHI cloning sites originally present. The modified vector is referred to as pAXneoR. The pAXneoR vector was linearized with SalI, the termini filled in using Klenow fragment of DNA polymerase to create blunt-ended molecules. The 2548 bp SmaI-XmI β-amyloid fragment was blunt-ligated into the vector using T4 ligase. The recombinant molecules were introduced into *E. coli* MC1061 by transformation and a clone displaying the proper orientation was amplified. A similar construction was made using the 695 8-amyloid sequences described by Kang et al. (supra) which places the 695 amyloid protein under control of the human β-actin promoter.

600 μg total DNA of pAXneo/751 8-amyloid or pAXneo/695 8-amyloid or an equal mass mixture of both plasmid constructs were introduced into 10$^7$ CHO cells by electroporation (Neumann, *J Membrane Biol* (1972) 10:279–290; Zimmerman, *Biophys J* (1973) 13:1005–1013) using a BTX Transfector 100, Bio-Rad sterile, disposal cuvettes and a custom built cuvette holder. G418-resistant cells receiving the exogenous DNA were selected by standard protocols (Southern, 1982, supra) using 500 μg/ml G418 from Gibco.

The pool of positively transfected cells resistant to G418 from each of the three transfections was characterized with respect to β-amyloid precursor protein expression. Approximately 2×10$^6$ cells from each pool containing 5 ml of serum-free medium were incubated at 37° C. for 48 hr. The conditioned media was removed and the protein precipitated by addition of trichloroacetic acid to a final concentration of 10%. Cells were harvested by scraping, washed in saline buffered with phosphate and resuspended in 50 ul of buffer for a 30-fold concentration. 25 ul of each sample was loaded onto a 12.5% polyacrylamide gel (Laemmli, *Nature* (1970) 277:680-685). The β-amyloid precursor was detected by Western blot analysis (Towbin, *Proc Nat'l Acad Sci USA* (1979) 76:4350-4354) using standard procedures and β-amyloid-specific polyclonal antibodies generated by recombinant vaccinia virus harboring the β-amyloid 751 cDNA as described in Example 3. Typically, the majority of the approximately 110,000 dalton β-amyloid precursor is found to be released into the culture media and very small amounts of the protein is cell-associated. This result is in keeping with the hypothesis of Allsop et al. (*Proc Natl Acad Sci USA* (1988) 85:2790-2794) proposing that the β-amyloid protein is a secreted prohormone. The apparent molecular weight of 110,000 daltons of the recombinantly expressed β-amyloid protein is similar to that observed by others (Dyrks, T., et al., *EMBO J* (1988) 7(4) 949-957) using in vitro transcription/translation systems.

Figure 15:
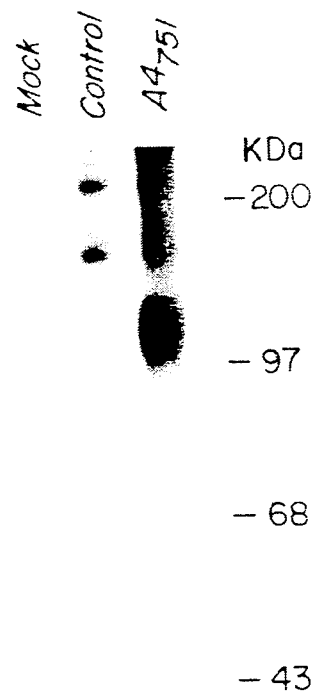
FIG. 15 shows the results of a Western blot analysis of the CV-1 cells producing the 751 amino acid β-amyloid protein using β-amyloid specific polyclonal antisera. The control is the pSC11 vaccinia virus lacking the β-amyloid coding sequence.

The β-amyloid 751 protein cloned into a vaccinia virus as described in Example 3 was also examined for the nature of β-amyloid protein expression. The purified recombinant virus was used to infect 10⁶ CV-1 cells at a MOI of 1 under serum-free conditions. 18 hr post infection with the virus, both cells and supernatants were harvested, subjected to polyacrylamide gel electrophoresis and Western blotting using the polyclonalantisera described above. As shown in FIG. 15, the β-amyloid 110,000 dalton protein was found to be present in the conditioned media versus associated with the cell.

EXAMPLE 7

Assay to Distinguish Genetic Variants of β-Amyloid-Related Protein mRNA Species

The ability to distinguish between genetic variants of β-amyloid-related protein mRNA species using oligonucleotide probes is demonstrated herein.

A diagnostic assay for Alzheimer's disease might take the form of distinguishing between two closely related genetic variants of β-amyloid-related proteins or their mRNAs, and quantitating the relative levels of expression of these proteins or mRNAs. FIG. 8 provides an example of the use of the invention sequences to provide a standard for the diagnostic assay.

Total cellular RNA or cytoplasmic RNA was prepared from human cells in culture or human brain tissue (Alzheimer's brain or normal brain) with or without removal of nuclei (cytoplasmic or total, respectively) by the guanidine thiocyanate/CsCl method as described by Maniatis et al. The samples corresponding to the numbering in FIG. 8 are: (1) total RNA from IMR-32 cells (ATCC #CCL127), a mixed neuroblastoma and fibroblast culture; (2) total RNA from MRC5 cells (ATCC #CCL171), a normal fibroblast; (3) total RNA from HeLa cells (ATCC #CCL2.2), an epitheloid cell; (4) cytoplasmic RNA from MRC5 cells; (5) cytoplasmic RNA from HeLa cells; (6) total RNA from HL-60 cells (ATCC #CCL240), a promyelocytic leukemia; (7) total RNA from HL-60 cells which have been treated with 12-tetra-decanoyl-phorbol-13-acetate to induce differentiation of the cells to macrophages; (8) total RNA from normal cerebellum samples; (9) total RNA from normal frontal cortex samples; (10) total RNA from an Alzheimer's individual's frontal cortex; and (11) total RNA from a normal parietal cortex. RNA was fractionated by oligo-dT cellulose chromatography, electrophoresed on a formaldehyde agarose gel, and blot-transferred to nitrocellulose (all as described in Maniatis et al.). Filters were baked, prehybridized and hybridized to the indicated probes according to standard protocols.

The probes indicated are: (1) Junction, a 30 base oligonucleotide #2733, specific for the Kang et al. sequence, as described above in the detailed description of the invention; (2) Insert, a 60 base oligonucleotide #2734 specific for the β-amyloid-relate described in FIG. 1, and as described above; and (3) an 1800 bp human actin cDNA insert, isolated from the plasmid pHFBA-1 (Ponte, P., et al., *Nuc Acids Res* (1984) 12:1687-1696. Oligonucleotide probes were end-labeled with [³²P]-dCTP by incubation with terminal transferase according to manufacturer's suggestions. Actin insert was radiolabeled with [³²p]-CTP by nick-translation. After hybridization, the filters hybridized to oligonucleotides were washed at 1×S.S.C., 55° C. The 5° C. Filters were then exposed to X-ray film to produce the autoradiogram shown. The insert probe detects the β-amyloid related protein mRNA described in FIG. 1 in all samples examined. The junction probe detects the β-amyloid-related mRNA described by Kang et al. in all cells except HeLa and MRC5. The actin probe is a control which is expected to hybridize to an abundant RNA in all cells.

EXAMPLE 8

Bacterial Expression of β-Amyloid-Related Protein (289-345)

A. Construction of Plasmid pAPCP125-2

A synthetic gene was assembled according to the teaching of Example 2 for β-amyloid-related protein 289-345) from three pairs of oligodeoxyribonucleotides (illustrated in FIG. 9D) utilizing *E. coli* preferred codon choice for highly expressed genes, and a hydroxylamine cleavage site (Asn-Gly) was inserted preceding amino acid 289 (Glu) to permit release of the polypeptide from a fusion protein. The expression vector pTRP83-1 was digested with restriction endonucleases EcoRI and HindIII and the linearized plasmid purified from a 0.6% agarose gel. Fifty μg of plasmid DNA and 200 μg of synthetic gene DNA were ligated using T4 DNA ligase and *E. coli* MC1061 was transformed with the ligation. Ampicillin-resistant colonies were grown overnight in L broth containing 100 μg/ml ampicillin and alkaline plasmid preps were made. The resulting plasmid DNA was digested with BamHI restriction endonuclease to confirm insertion of the gene within the vector by release of an approximately 350 bp fragment. One plasmid receiving the synthetic gene insert was designated pAPCP125-2.

B. Expression of β-Amyloid-Related Fusion Polypeptide (289-345)

The plasmid pAPCP125-2 is designed to express a 74 amino acid β-galactosidase-threonine-β-amyloid-related fusion protein under the control of the *E. coli* tryptophan promoter/operator. *E. coli* strain W3110 is transformed with plasmid pAPCP125-2 and one of the resulting ampicillin resistant colonies is grown as described in Example 2. Expression is induced by the addition of 3β-indoleacrylic acid at a final concentration of 25 μg/ml. After 5 hrs induction, a 1 ml aliquot of cells is withdrawn from the culture, harvested by centrifugation, then boiled in 100 μl of Laemmli protein sample buffer for electrophoresis through a 16% SDS-polyacrylamide gel by standard methodologies. Assessment of inclusion body formation is made by phase contrast microscopy (1000×). Expression levels are estimated by Coomassie blue staining of the gel followed by densitometer scan to quantitate the intensity of protein bands. Cells to be used for protein purification are harvested by centrifugation, washed with 10 mM Tris-HCl, pH 7.5, and the cell pellet frozen at −20° C. until needed.

C. Purification of Beta-qal-thr-β-amyloid-related Protein (289-345)

The fusion protein is purified as described for the β-gal-thr-β-amyloid-related (655-751) fusion protein (Example 2) in the absence of PMSF and aprotinin. A series of washes from 2 M urea to 4 M urea removes other proteins and further enriches fusion protein found in inclusion bodies. If further purification is desired, the fusion protein is solubilized in 6-8 M urea, and a gel filtration or ion exchange chromatography step is included. If not, the fusion protein is solubilized in 6 M guanidium hydrochloride with hydroxylamine under the conditions described by Moks et al., *Biochem* (1987) 26:5239-5244 for cleavage between the Asn and Gly residues releasing β-amyloid-related protein (289-345) with a Gly residue at its amino-terminus. The cleaved peptides are purified by reversed phase high pressure liquid chromatography, ion exchange or gel filtration chromatography. The purified β-amyloid-related protein is then reduced and reoxidized by methods described by Tan and Kaiser, *J Org Chem* (1976) 41:2787 and *Biochemistry* (1977) 16:1531-1541, to reform disulfide bonds between the six Cys residues. Successful reoxidation of bovine pancreatic trypsin inhibitor (aprotinin) also containing six Cys residues and produced in *E. coli* has been accomplished by these methods (von Wilcken-Bergmann et al., *EMBO* (1986) 5:3219-3225).

EXAMPLE 9

Construction and Expression of the Inhibitor Protein

DNA sequences coding for each of the two chimeric proteins were assembled from synthetic oligonucleotides. The sequences of the oligonucleotides used are shown in FIG. 16. The sequence of the phoA signal peptide (FIG. 16B) is from Kikuchi et al. (supra), the sequence for ompA signal peptide (FIG. 16A) is from Beck and Bremer, (supra). Each oligonucleotide was treated with kinase (except for the 2 outside 5′ ends).

All 8 oligonucleotides encoding either the phoA or ompA fusions were mixed together and treated with ligase. Analytical gels showed a new band of the expected length (~250 bp). The ligated constructs were then ligated into the NdeI-HindIII sites of the vector pTRP233. The ligated vectors were transfected into *E. coli* strain MC1061 and Amp$^R$ colonies selected. Plasmid minipreps showed recombinant plasmids with the correct restriction map. Miniprep DNA was used to transfect strains W3110 and JE5505. Small scale cultures of each of the three strains were grown and induced with IAA overnight. Culture supernatants were examined for trypsin inhibitory activity. Trypsin is assayed for its ability to hydrolyze the synthetic substrate N-benzoyl-D-arginine-p-nitroaniline to release p-nitroaniline (pNA). The release of pNA as a function of time is easily monitored in a spectrophotometer and can be quantitated to measure trypsin activity. The inhibitor is detected in this assay by virtue of its ability to bind to trypsin and prevent hydrolysis of the substrate by trypsin. Inhibitory activity was detected in the culture medium for both ompA and phoA constructs in JE5505 but not W3110 or MC1061. Expression levels appeared to be higher with the phoA construct and so only this construct was used for subsequent experiments.

A time course study was conducted in which levels of inhibitor in the medium were assayed and rates of synthesis of the inhibitor were monitored by $^{35}$S-methionine incorporation into inhibitor protein. This study showed that synthesis declined to zero between 4 and 6 hrs after induction with IAA while inhibitor protein accumulated in the medium out to 8 hrs post-induction. This lag is presumed to represent the time required for protein to diffuse from the periplasm through the outer membrane into the medium. Levels of inhibitor in the medium appeared to remain stable from 8 to 24 hrs post-induction.

EXAMPLE 10

Purification of Inhibitor Protein

A 5 liter culture of *E. coli* JE5505 transformed with the phoA construct was grown overnight, induced at OD$_{550}$=0.1, and harvested at 8 hrs after induction with IAA. Cells were centrifuged out and discarded The supernatant was filtered through 8 μm and 0.45 μm filters and passed through a trypsin Sepharose affinity column (total 10 ml Sepharose, 6 mg/ml trypsin on Sepharose, 5 ml/min flow rate, 4° C.). The column was washed with 0.1 M sodium acetate buffer, pH 4, containing 0.3 M sodium chloride (NaCl) and 0.01 M calcium chloride (CaCl$_2$) to remove nonspecifically bound protein. The inhibitor was eluted with a buffer of 0.1 M hydrochloric acid-0.5 M NaCl-0.01 M CaCl$_2$, pH 1.25. Alternatively, rather than using trypsin affinity column as the affinity matrix, a trypsin bead slurry may be employed. To 5 liters of the *E. coli* JE5505 supernatant, about 20 ml of a trypsin Sepharose bead slurry were added and stirred gently with a mixer (at 300 rpm, 1 hr, room temperature). The mixture was decanted into a scintered glass funnel and the liquid aspirated from the beads. Using approximately 4 liters of 20 mM Tris-HCl, pH 7.5, the beads were re-equilibrated and then washed with 0.1 M acetic acid-0.3 M NaCl, pH 4.5. The beads were re-equilibrated using 20 mM Tris-HCl, pH 7.5 and then the protease inhibitor was eluted using about 80 mls of 0.1 M HCl-0.5 M NaCl, pH 1.25. The eluate was neutralized using approximately 2.5 mls of 2 M Tris base, pH 10.0.

The trypsin affinity column eluate was injected onto a Jones Chromatography APEX-WP® butyl HPLC column (1 cm ID×25 cm length) equilibrated in 20% acetonitrile-0.1% trifluoroacetic acid-80% water. A linear gradient to 60% acetonitrile/0.1% TFA in H$_2$O was run to eluate the inhibitor. The inhibitor elutes in a major peak (peak 4) and a minor peak (peak 2). Both are active in the trypsin inhibition assay, both appear homogeneous on the protein sequencer (40 cycles for peak 4, 49 cycles for peak 2) and both have the amino acid composition expected for the A4 inhibitor. Treatment of peak 2 with 10 mM DTT (dithiothreitol) causes partial conversion of peak 2 to peak 4, suggesting that peak 2 may rise by oxidation of methionine. In each case the endogenous *E. coli* signal peptidase had cleaved the chimeric protein at the expected site as shown by the arrows in FIG. 16. Mass spectrometric (MS) analysis indicates that peak 4 has a molecular mass of 6,267 daltons, very close to the predicted value of 6,267.7 for full length A4i with 3 disulfide bridges. Since each S—S bridge formed results in loss of 2 H+(=2 daltons), the number of S—S can be assessed. Peak 2 gives a heterogeneous peak in MS about 80 daltons greater than peak 4, consistent with oxidation. The acid conditions used to elute the protein from the trypsin-Sepharose affinity column will promote oxidation of methionine, however, peak 2 formation is minimized by rapid neutralization using a buffered solution, such as, for example, 2 M Tris base having a pH in the range of about 8 to about 11, preferably pH 10.0, after elution from the trypsin-Sepharose affinity column.

EXAMPLE 11

A4 Inhibitory Activity

The effects of A4 inhibitor on serine- and thiol- proteases were examined as follows: trypsin (17,000 units/mg from porcine pancreas), factor Xa and β-thrombin (gifts from Dr. Iwanagu, Kyushu University, Fukuoka, Japan), tryptase and chymase (both from rat peritoneal mast cells purified as described in Kido et al., *Arch Biochem Biophys* 239:436–443 (1985)), α-chymotrypsin (0.75 U/mg from bovine pancreas), elastase (33 U/mg from porcine pancreas), papain, cathepsin B (from rat liver purified as described in Towatari et al., *Eur J Biochem* 102:279-289 (1979)), plasmin (0.16 U/mg from human plasma), urokinase (0.75 U/mg from human kidney cells, Sigma Chemical Co.), tissue kallikrein (50 U/mg from porcine pancreas) or plasma kallikrein (9.4 U/mg from human plasma) was preincubated with various concentrations of the inhibitor in a total volume of 1.5 ml of buffer containing bovine serum albumin (0.1 mg/ml). The buffers used were as follows: 0.1 M Tris-HCl, pH 7.5, for trypsin, plasmin and urokinase; 0.1 M Tris-HCl, pH 8.0, for chymase and α-chymotrypsin; 0.1 M Tris-HCl, pH 8.0, containing 10 mM CaCl$_2$ for factor Xa and α-thrombin; 0.1 M Tris-HCl, pH 8.5, for tryptase M; 0.1 M Tris-HCl, pH 7.8, for plasma and tissue kallikrein; 0.1 M Tris-HCl, pH 7.0 for elastase; 50 mM acetate, pH 6.0, containing 1 mM EDTA and 4 mM cysteine for papain and cathepsin B. After preincubation for 5 min at 25° C., 7.5 μl of 20 mM concentrations of the fluorogenic substrate shown in Table I were added and the residual activity of each protease was measured in a quartz cuvette maintained thermostatically at 25° C. The amount of 7-amino-4-methylcoumarin liberated from the substrates was determined fluorometrically with excitation and emission wavelengths of 380 nm and 460 nm, respectively, in a Hitachi fluorescence spectrophotometer, 650–10MS model, as reported in Kido et al. (1988), supra. Protein concentration was determined with bicinchoninic acid protein assay reagent as described by Smith et al., *Anal. Biochem.* 150:76–85 (1985).

The Ki values of the A4 inhibitor for various proteases was determined from a Lineweaver-Burk plot of the initial rate of hydrolysis of substrate and are shown in Table I.

TABLE I

| Protease | Substrate[a] | pH | Ki value nM |
|---|---|---|---|
| Trypsin | Boc—Phe—Ser—Arg—MCA | 7.5 | 2.7 |
| Tryptase M | Boc—Phe—Ser—Arg—MCA | 8.5 | 0.22 |
| Factor Xa | Boc—Ile—Glu—Gly—Arg—MCA | 8.0 | 257.0 |
| α-Thrombin | Boc—Val—Pro—Arg—MCA | 8.0 | NI[b] |
| Chymase | Suc[c]—Leu—Leu—Val—Tyr—MCA | 8.0 | NI |
| α-Chymotrypsin | Suc—Leu—Leu—Val—Tyr—MCA | 8.0 | 8.5 |
| Elastase | Suc—Ala—Pro—Ala—MCA | 7.0 | NI |
| Plasmin | Boc—Val—Leu—Lys—MCA | 7.5 | 0.075 |
| Urokinase | Glt—Gly—Arg—MCA (Glt?) | 7.5 | NI |
| Plasma kallikrein | Z[d]—Phe—Arg—MCA | 7.8 | 73.9 |
| Tissue kallikrein | Pro—Phe—Arg—MCA | 7.8 | 28.4 |
| Papain | Z—Phe—Arg—MCA | 6.0 | NI |
| Cathepsin B | Z—Phe—Arg—MCA | 6.0 | NI |

[a]Provided by the Protein Research Foundation, Osaka, Japan.
[b]NI, no inhibition at a concentration of 1 μM A4 inhibitor.
[c]Suc—, succinyl-.
[d]Z—; benzyloxycarbonyl.

This A4 inhibitor strongly inhibited plasmin (Ki=7.5×10$^{-11}$M) from human serum and tryptase M (Ki'2.2×10$^{-10}$M) from rat mast cells. It also inhibited pancreatic trypsin (Ki=2.7×10$^{-9}$M), α-chymotrypsin (Ki=8.5×10$^{-9}$M) and plasma and tissue kallikrein (Ki =7.4×10$^{-8}$M and 2.8×10$^{-8}$M, respectively) but did not inhibit chymase or pancreatic elastase. It inhibited factor Xa (Ki=2.57×10$^{-6}$M) slightly, but did not inhibit α-thrombin, urokinase, papain or cathepsin B.

EXAMPLE 12

Trypsin Inhibition

Trypsin (30 pM) was preincubated with various concentrations (3–24 pM) of purified A4i inhibitor in 0.1 M Tris-HCl, pH 7.5, containing bovine serum albumin (0.1 mg/ml) at 25° C. for 5 min. Residual activities of trypsin were measured with Boc-Phe-Ser-Arg-MCA as substrate.

The plot of the inhibition of trypsin by the purified A4i inhibitor indicated a 1:1 molar reaction of the A4i inhibitor with trypsin.

EXAMPLE 13

Pharmaceutical IV Composition

A solution of A4i and/or analogs thereof as described above in a phosphate buffered physiological saline solution which contains 0.001% of Tween 80 red 0.01–1% of albumin or mannitol, will provide an intravenous formulation suitable for injection.

EXAMPLE 14

Pharmaceutical Topical Composition

Pharmaceutically effective topical compositions of the invention are preferably in the form of dressings. Such dressings are external pharmaceutical applications resembling ointments which are generally used as coverings for abraded tissues. The A4i protein and/or analogs thereof can be added to a petroleum gauze which is a sterile dressing prepared by adding sterile molten white petroleum to pre-cut sterile gauze in a ratio of 60 grams of petroleum to 20 grams of gauze. The A4i protein or analog can be added to the gauze in any given amount depending on the needs of the particular patient. However, such a protein is generally added in a relatively small amount such as in the range of about 1 to 10 grams per 20 grams of gauze and 60 grams of petroleum. The topical antibacterial components can be added to the dressing to aid in preventing infection.

EXAMPLE 15

Topical Creams

Topical creams useful in treating wounds, and abraded tissues and in providing for transdermal and transmucousal penetration of A4i proteins and analogs thereof can be prepared by mixing various inert excipient materials with the A4i protein and/or analogs thereof generally in a ratio of about 90–99% excipient by weight to 1–10% protein by weight. The excipient materials are preferably demulcents which are protective agents employed primarily to alleviate irritation particularly on mucous membranes and abraded tissue. Useful demulcents include mucilages, gums, dextrins, starches, certain sugars, and polymeric polyhydric glycols. Mucous itself is a natural demulcent and synthetic mucous creams are known to those skilled in the art which can serve as the excipient base material to be combined with the protein for topical application.

EXAMPLE 16

Ophthalmic Formulations

Ophthalmic formulations can be prepared containing the A4i proteins and/or analogs thereof for the treatment of abraded ocular tissues. As such ocular formulations can be prepared by adding 1–10% by weight of the A4i protein and/or analogs thereof to a conventional wetting solution for contact lenses. Such solutions are comprised of water and polyvinyl alcohol as a demulcent that helps protect the eye from irritation generally caused by contact lenses.

While preferred embodiments of making and using the invention have been described, it will be appreciated that various changes and modifications can be made without departing from the invention.

The following cultures have been deposited with the American Type Culture Collection (ATCC), Rockville, Md., USA for patent purposes. Bacteriophage phages λSM2, λSM2W9, and λAPCP168i4 were deposited under the conditions specified by the Budapest Treaty on the International Recognition of the Deposit of Microorganisms (Budapest Treaty).

| Culture | Accession No. | Deposit Date |
|---|---|---|
| λSM2 | 40279 | 13 November 1986 |
| SM2W4 | 40299 | 29 December 1986 |
| SM2W3 | 40300 | 29 December 1986 |
| λSM2W9 | 40304 | 29 January 1987 |
| λACPC168i4 | 40347 | 1 July 1987 |

Availability of the deposited strains are not to be construed as a license to practice the invention in contravention of the rights granted under the authority of any government in accordance with its patent laws.

We claim:

1. A method of treating an individual having excessive activity of serine proteases, comprising:
   administering to the individual in need thereof a pharmaceutically effective amount of the composition, comprising:
   a pharmaceutically acceptable carrier; and
   a protein analog wherein the amino acid corresponding to arginine at position 13 in the sequence GluValCysSerGluGlnAlaGluThrGlyProCysArg$_{13}$AlaMet
IleSerArgTrpTyrPheAspValThrGluGlyLysCysAla
ProPhePheTyrGlyGlyCysGlyGlyAsnArgAsnAsnPhe
AspThrGluGluTyrCysMetAlaValCysGlySerAlaIle is substituted with a neutral hydrophobic amino acid.

2. The method as claimed in claim 1, wherein the serine protease inhibited by the protein analog is elastase and the neutral hydrophobic amino acids is valine.

3. The method as claimed in claim 1, wherein the excessive activity of serine proteases is associated with emphysema.

* * * * *